(12) United States Patent
Honnorat et al.

(10) Patent No.: US 9,766,253 B2
(45) Date of Patent: Sep. 19, 2017

(54) FIBROBLAST GROWTH FACTOR RECEPTORS AS DIAGNOSTIC MARKERS OF ACQUIRED SENSORY NEURONOPATHIES

(71) Applicants: INSTITUT NATIONAL DE LA SANTE ET DE LA RECHERCHE MEDICALE (INSERM), Paris (FR); CENTRE NATIONAL DE LA RECHERCHE SCIENTIFIQUE, Paris (FR); UNIVERSITE JEAN MONNET, Saint-Etienne (FR); UNIVERSITE CLAUDE BERNARD LYON 1, Villeurbanne (FR); HOSPICES CIVILS DE LYON, Lyons (FR); CENTRE HOSPITALIER UNIVERSITAIRE DE SAINT ETIENNE, Saint Etienne (FR)

(72) Inventors: Jerome Marc Claude Honnorat, Lyons (FR); Jean-Christophe Antoine, Saint-etienne (FR); Jean-Philippe Camdessanche, Saint-etienne (FR); Nadia Boutahar, Saint-etienne (FR); Veronique Annie Rogemond, Bron (FR)

(73) Assignees: Institut National de la Sante et de la Recherche Medicale (INSERM), Paris (FR); Centre National de la Recherche Scientifique, Paris (FR); Universite Jean Monnet, Saint-Etienne (FR); Universite Claude Bernard Lyon 1, Villeurbanne (FR); Hospices Civils de Lyon, Lyons (FR); Centre Hospitalier Universitaire de Saint Etienne, Saint Etienne (FR)

( * ) Notice: Subject to any disclaimer, the term of this patent is extended or adjusted under 35 U.S.C. 154(b) by 0 days.

(21) Appl. No.: 14/417,918

(22) PCT Filed: Jun. 28, 2013

(86) PCT No.: PCT/EP2013/063720
§ 371 (c)(1),
(2) Date: Jan. 28, 2015

(87) PCT Pub. No.: WO2014/019781
PCT Pub. Date: Feb. 6, 2014

(65) Prior Publication Data
US 2015/0192594 A1    Jul. 9, 2015

(30) Foreign Application Priority Data
Jul. 30, 2012 (EP) .................... 12305933

(51) Int. Cl.
*G01N 33/68* (2006.01)
*G01N 33/564* (2006.01)
*A61K 31/137* (2006.01)
*A61K 31/436* (2006.01)
*A61K 31/519* (2006.01)
*A61K 31/52* (2006.01)
*A61K 31/675* (2006.01)
*A61K 38/13* (2006.01)
*C07K 16/28* (2006.01)
*A61K 31/365* (2006.01)

(52) U.S. Cl.
CPC ....... *G01N 33/6896* (2013.01); *A61K 31/137* (2013.01); *A61K 31/365* (2013.01); *A61K 31/436* (2013.01); *A61K 31/519* (2013.01); *A61K 31/52* (2013.01); *A61K 31/675* (2013.01); *A61K 38/13* (2013.01); *C07K 16/2887* (2013.01); *G01N 33/564* (2013.01); *G01N 2333/71* (2013.01); *G01N 2800/28* (2013.01); *G01N 2800/52* (2013.01)

(58) Field of Classification Search
None
See application file for complete search history.

(56) References Cited

FOREIGN PATENT DOCUMENTS

EP    2 444 811 A1    4/2012

OTHER PUBLICATIONS

Koziczak et al., Oncogene, 2004; 23: 3501-3508.*
Mutoh et al., Arch Neurol. 2005; 62 :1612-1615.*
Hoch et al., Nature Medicine, 2001; 7: 365-368.*
Lemmon and Schlessinger, Cell. 2010; 141: 1117-1134.*
Antoine et al., J Neurol Neurosurg Psychiatry 2015; 86: 1347-1355.*
Sewell, Immunology, 2002; 107: 387-393.*
He et al., "Inhibition of tumor growth with a vaccine based on xenogeneic homologous fibroblast growth factor receptor-1 in mice", The Journal of Biological Chemistry, Jun. 13, 2004, The Journal of Biological Chemistry, pp. 21831-21836, vol. 278, No. 24.
Mukherjee et al., "Co-ordination of TGF-beta and FGF signaling pathways in bone organ cultures", Mechanisms of Development, Apr. 2005, pp. 557-571, vol. 122, No. 4.
Fabien et al., "[Antireceptor and antichannel autoantibodies]", Pathologie-Biologie, May 2006, pp. 309-316, vol. 54, No. 5.
Kuntzer et al., "Climincal features and pathophysiological basis of sensory neuronopathies (ganglionopathies)", Muscle & Nerve, Sep. 2004, pp. 255-268, vol. 30, No. 3.
Sieb, Joern, "Myasthenia gravis: emerging new therapy options", Current Opinion in Pharmacology, Jun. 2005, pp. 303-307, vol. 5, No. 3.
Anderson et al., "Autoantibodies in paraneoplastic syndromes associated with small-cell lung cancer", Neurology, Sep. 1988, pp. 1391-1398, vol. 38, No. 9.

(Continued)

*Primary Examiner* — Christina Borgeest
(74) *Attorney, Agent, or Firm* — Whitham Curtis & Cook, PC

(57) ABSTRACT

The present invention relates to the diagnosis of acquired sensory neuronopathies (SNN), and to the treatment of these disorders.

5 Claims, 3 Drawing Sheets

(56) References Cited

OTHER PUBLICATIONS

Camdessanche et al., "The pattern and diagnostic criteria of sensory neuronopathy: a case-control study", Brain: A Journal of Neurology, Jul. 2009, pp. 1723-1733, vol. 132, No. Pt 7.
Sghirlanzoni et al., "Sensory neuron diseases", Lancet Neurology, Jun. 2005, pp. 349-361, vol. 4, No. 6.

* cited by examiner

```
                            SEQUENCE LISTING

<160> NUMBER OF SEQ ID NOS: 21

<210> SEQ ID NO 1
<211> LENGTH: 822
<212> TYPE: PRT
<213> ORGANISM: Homo sapiens

<400> SEQUENCE: 1

Met Trp Ser Trp Lys Cys Leu Leu Phe Trp Ala Val Leu Val Thr Ala
1               5                   10                  15

Thr Leu Cys Thr Ala Arg Pro Ser Pro Thr Leu Pro Glu Gln Ala Gln
                20                  25                  30

Pro Trp Gly Ala Pro Val Glu Val Glu Ser Phe Leu Val His Pro Gly
            35                  40                  45

Asp Leu Leu Gln Leu Arg Cys Arg Leu Arg Asp Asp Val Gln Ser Ile
        50                  55                  60

Asn Trp Leu Arg Asp Gly Val Gln Leu Ala Glu Ser Asn Arg Thr Arg
65                  70                  75                  80

Ile Thr Gly Glu Glu Val Glu Val Gln Asp Ser Val Pro Ala Asp Ser
                85                  90                  95

Gly Leu Tyr Ala Cys Val Thr Ser Ser Pro Ser Gly Ser Asp Thr Thr
            100                 105                 110

Tyr Phe Ser Val Asn Val Ser Asp Ala Leu Pro Ser Ser Glu Asp Asp
        115                 120                 125

Asp Asp Asp Asp Asp Ser Ser Ser Glu Glu Lys Glu Thr Asp Asn Thr
130                 135                 140

Lys Pro Asn Arg Met Pro Val Ala Pro Tyr Trp Thr Ser Pro Glu Lys
145                 150                 155                 160

Met Glu Lys Lys Leu His Ala Val Pro Ala Ala Lys Thr Val Lys Phe
                165                 170                 175

Lys Cys Pro Ser Ser Gly Thr Pro Asn Pro Thr Leu Arg Trp Leu Lys
            180                 185                 190

Asn Gly Lys Glu Phe Lys Pro Asp His Arg Ile Gly Gly Tyr Lys Val
        195                 200                 205

Arg Tyr Ala Thr Trp Ser Ile Ile Met Asp Ser Val Val Pro Ser Asp
    210                 215                 220

Lys Gly Asn Tyr Thr Cys Ile Val Glu Asn Glu Tyr Gly Ser Ile Asn
225                 230                 235                 240

His Thr Tyr Gln Leu Asp Val Val Glu Arg Ser Pro His Arg Pro Ile
                245                 250                 255

Leu Gln Ala Gly Leu Pro Ala Asn Lys Thr Val Ala Leu Gly Ser Asn
            260                 265                 270

Val Glu Phe Met Cys Lys Val Tyr Ser Asp Pro Gln Pro His Ile Gln
        275                 280                 285

Trp Leu Lys His Ile Glu Val Asn Gly Ser Lys Ile Gly Pro Asp Asn
    290                 295                 300

Leu Pro Tyr Val Gln Ile Leu Lys Thr Ala Gly Val Asn Thr Thr Asp
305                 310                 315                 320

Lys Glu Met Glu Val Leu His Leu Arg Asn Val Ser Phe Glu Asp Ala
                325                 330                 335

Gly Glu Tyr Thr Cys Leu Ala Gly Asn Ser Ile Gly Leu Ser His His
            340                 345                 350
```

```
Ser Ala Trp Leu Thr Val Leu Glu Ala Leu Glu Glu Arg Pro Ala Val
        355                 360                 365

Met Thr Ser Pro Leu Tyr Leu Glu Ile Ile Ile Tyr Cys Thr Gly Ala
370                 375                 380

Phe Leu Ile Ser Cys Met Val Gly Ser Val Ile Val Tyr Lys Met Lys
385                 390                 395                 400

Ser Gly Thr Lys Lys Ser Asp Phe His Ser Gln Met Ala Val His Lys
                405                 410                 415

Leu Ala Lys Ser Ile Pro Leu Arg Arg Gln Val Thr Val Ser Ala Asp
            420                 425                 430

Ser Ser Ala Ser Met Asn Ser Gly Val Leu Leu Val Arg Pro Ser Arg
        435                 440                 445

Leu Ser Ser Ser Gly Thr Pro Met Leu Ala Gly Val Ser Glu Tyr Glu
    450                 455                 460

Leu Pro Glu Asp Pro Arg Trp Glu Leu Pro Arg Asp Arg Leu Val Leu
465                 470                 475                 480

Gly Lys Pro Leu Gly Glu Gly Cys Phe Gly Gln Val Val Leu Ala Glu
                485                 490                 495

Ala Ile Gly Leu Asp Lys Asp Lys Pro Asn Arg Val Thr Lys Val Ala
            500                 505                 510

Val Lys Met Leu Lys Ser Asp Ala Thr Glu Lys Asp Leu Ser Asp Leu
        515                 520                 525

Ile Ser Glu Met Glu Met Met Lys Met Ile Gly Lys His Lys Asn Ile
    530                 535                 540

Ile Asn Leu Leu Gly Ala Cys Thr Gln Asp Gly Pro Leu Tyr Val Ile
545                 550                 555                 560

Val Glu Tyr Ala Ser Lys Gly Asn Leu Arg Glu Tyr Leu Gln Ala Arg
                565                 570                 575

Arg Pro Pro Gly Leu Glu Tyr Cys Tyr Asn Pro Ser His Asn Pro Glu
            580                 585                 590

Glu Gln Leu Ser Ser Lys Asp Leu Val Ser Cys Ala Tyr Gln Val Ala
        595                 600                 605

Arg Gly Met Glu Tyr Leu Ala Ser Lys Lys Cys Ile His Arg Asp Leu
    610                 615                 620

Ala Ala Arg Asn Val Leu Val Thr Glu Asp Asn Val Met Lys Ile Ala
625                 630                 635                 640

Asp Phe Gly Leu Ala Arg Asp Ile His His Ile Asp Tyr Tyr Lys Lys
                645                 650                 655

Thr Thr Asn Gly Arg Leu Pro Val Lys Trp Met Ala Pro Glu Ala Leu
            660                 665                 670

Phe Asp Arg Ile Tyr Thr His Gln Ser Asp Val Trp Ser Phe Gly Val
        675                 680                 685

Leu Leu Trp Glu Ile Phe Thr Leu Gly Gly Ser Pro Tyr Pro Gly Val
    690                 695                 700

Pro Val Glu Glu Leu Phe Lys Leu Leu Lys Glu Gly His Arg Met Asp
705                 710                 715                 720

Lys Pro Ser Asn Cys Thr Asn Glu Leu Tyr Met Met Met Arg Asp Cys
                725                 730                 735

Trp His Ala Val Pro Ser Gln Arg Pro Thr Phe Lys Gln Leu Val Glu
            740                 745                 750

Asp Leu Asp Arg Ile Val Ala Leu Thr Ser Asn Gln Glu Tyr Leu Asp
        755                 760                 765

Leu Ser Met Pro Leu Asp Gln Tyr Ser Pro Ser Phe Pro Asp Thr Arg
```

```
                 770                 775                 780
Ser Ser Thr Cys Ser Ser Gly Glu Asp Ser Val Phe Ser His Glu Pro
785                 790                 795                 800

Leu Pro Glu Glu Pro Cys Leu Pro Arg His Pro Ala Gln Leu Ala Asn
                805                 810                 815

Gly Gly Leu Lys Arg Arg
            820

<210> SEQ ID NO 2
<211> LENGTH: 731
<212> TYPE: PRT
<213> ORGANISM: Homo sapiens

<400> SEQUENCE: 2

Met Trp Ser Trp Lys Cys Leu Leu Phe Trp Ala Val Leu Val Thr Ala
1               5                   10                  15

Thr Leu Cys Thr Ala Arg Pro Ser Pro Thr Leu Pro Glu Gln Asp Ala
                20                  25                  30

Leu Pro Ser Ser Glu Asp Asp Asp Asp Asp Asp Ser Ser Ser Glu
            35                  40                  45

Glu Lys Glu Thr Asp Asn Thr Lys Pro Asn Pro Val Ala Pro Tyr Trp
50                  55                  60

Thr Ser Pro Glu Lys Met Glu Lys Lys Leu His Ala Val Pro Ala Ala
65                  70                  75                  80

Lys Thr Val Lys Phe Lys Cys Pro Ser Ser Gly Thr Pro Asn Pro Thr
                85                  90                  95

Leu Arg Trp Leu Lys Asn Gly Lys Glu Phe Lys Pro Asp His Arg Ile
            100                 105                 110

Gly Gly Tyr Lys Val Arg Tyr Ala Thr Trp Ser Ile Ile Met Asp Ser
        115                 120                 125

Val Val Pro Ser Asp Lys Gly Asn Tyr Thr Cys Ile Val Glu Asn Glu
    130                 135                 140

Tyr Gly Ser Ile Asn His Thr Tyr Gln Leu Asp Val Val Glu Arg Ser
145                 150                 155                 160

Pro His Arg Pro Ile Leu Gln Ala Gly Leu Pro Ala Asn Lys Thr Val
                165                 170                 175

Ala Leu Gly Ser Asn Val Glu Phe Met Cys Lys Val Tyr Ser Asp Pro
            180                 185                 190

Gln Pro His Ile Gln Trp Leu Lys His Ile Glu Val Asn Gly Ser Lys
        195                 200                 205

Ile Gly Pro Asp Asn Leu Pro Tyr Val Gln Ile Leu Lys Thr Ala Gly
    210                 215                 220

Val Asn Thr Thr Asp Lys Glu Met Glu Val Leu His Leu Arg Asn Val
225                 230                 235                 240

Ser Phe Glu Asp Ala Gly Glu Tyr Thr Cys Leu Ala Gly Asn Ser Ile
                245                 250                 255

Gly Leu Ser His His Ser Ala Trp Leu Thr Val Leu Glu Ala Leu Glu
            260                 265                 270

Glu Arg Pro Ala Val Met Thr Ser Pro Leu Tyr Leu Glu Ile Ile Ile
        275                 280                 285

Tyr Cys Thr Gly Ala Phe Leu Ile Ser Cys Met Val Gly Ser Val Ile
    290                 295                 300

Val Tyr Lys Met Lys Ser Gly Thr Lys Lys Ser Asp Phe His Ser Gln
305                 310                 315                 320
```

```
Met Ala Val His Lys Leu Ala Lys Ser Ile Pro Leu Arg Arg Gln Val
                325                 330                 335
Thr Val Ser Ala Asp Ser Ser Ala Ser Met Asn Ser Gly Val Leu Leu
                340                 345                 350
Val Arg Pro Ser Arg Leu Ser Ser Ser Gly Thr Pro Met Leu Ala Gly
                355                 360                 365
Val Ser Glu Tyr Glu Leu Pro Glu Asp Pro Arg Trp Glu Leu Pro Arg
            370                 375                 380
Asp Arg Leu Val Leu Gly Lys Pro Leu Gly Glu Gly Cys Phe Gly Gln
385                 390                 395                 400
Val Val Leu Ala Glu Ala Ile Gly Leu Asp Lys Asp Lys Pro Asn Arg
                405                 410                 415
Val Thr Lys Val Ala Val Lys Met Leu Lys Ser Asp Ala Thr Glu Lys
                420                 425                 430
Asp Leu Ser Asp Leu Ile Ser Glu Met Glu Met Met Lys Met Ile Gly
            435                 440                 445
Lys His Lys Asn Ile Ile Asn Leu Leu Gly Ala Cys Thr Gln Asp Gly
                450                 455                 460
Pro Leu Tyr Val Ile Val Glu Tyr Ala Ser Lys Gly Asn Leu Arg Glu
465                 470                 475                 480
Tyr Leu Gln Ala Arg Arg Pro Pro Gly Leu Glu Tyr Cys Tyr Asn Pro
                485                 490                 495
Ser His Asn Pro Glu Glu Gln Leu Ser Ser Lys Asp Leu Val Ser Cys
            500                 505                 510
Ala Tyr Gln Val Ala Arg Gly Met Glu Tyr Leu Ala Ser Lys Lys Cys
                515                 520                 525
Ile His Arg Asp Leu Ala Ala Arg Asn Val Leu Val Thr Glu Asp Asn
            530                 535                 540
Val Met Lys Ile Ala Asp Phe Gly Leu Ala Arg Asp Ile His His Ile
545                 550                 555                 560
Asp Tyr Tyr Lys Lys Thr Thr Asn Gly Arg Leu Pro Val Lys Trp Met
                565                 570                 575
Ala Pro Glu Ala Leu Phe Asp Arg Ile Tyr Thr His Gln Ser Asp Val
                580                 585                 590
Trp Ser Phe Gly Val Leu Leu Trp Glu Ile Phe Thr Leu Gly Gly Ser
            595                 600                 605
Pro Tyr Pro Gly Val Pro Val Glu Glu Leu Phe Lys Leu Leu Lys Glu
            610                 615                 620
Gly His Arg Met Asp Lys Pro Ser Asn Cys Thr Asn Glu Leu Tyr Met
625                 630                 635                 640
Met Met Arg Asp Cys Trp His Ala Val Pro Ser Gln Arg Pro Thr Phe
                645                 650                 655
Lys Gln Leu Val Glu Asp Leu Asp Arg Ile Val Ala Leu Thr Ser Asn
                660                 665                 670
Gln Glu Tyr Leu Asp Leu Ser Met Pro Leu Asp Gln Tyr Ser Pro Ser
            675                 680                 685
Phe Pro Asp Thr Arg Ser Ser Thr Cys Ser Ser Gly Glu Asp Ser Val
            690                 695                 700
Phe Ser His Glu Pro Leu Pro Glu Glu Pro Cys Leu Pro Arg His Pro
705                 710                 715                 720
Ala Gln Leu Ala Asn Gly Gly Leu Lys Arg Arg
                725                 730
```

```
<210> SEQ ID NO 3
<211> LENGTH: 821
<212> TYPE: PRT
<213> ORGANISM: Homo sapiens

<400> SEQUENCE: 3

Met Val Ser Trp Gly Arg Phe Ile Cys Leu Val Val Thr Met Ala
1               5                   10                  15

Thr Leu Ser Leu Ala Arg Pro Ser Phe Ser Leu Val Glu Asp Thr Thr
                20                  25                  30

Leu Glu Pro Glu Glu Pro Thr Lys Tyr Gln Ile Ser Gln Pro Glu
            35                  40                  45

Val Tyr Val Ala Ala Pro Gly Glu Ser Leu Glu Val Arg Cys Leu Leu
    50                  55                  60

Lys Asp Ala Ala Val Ile Ser Trp Thr Lys Asp Gly Val His Leu Gly
65                  70                  75                  80

Pro Asn Asn Arg Thr Val Leu Ile Gly Glu Tyr Leu Gln Ile Lys Gly
                85                  90                  95

Ala Thr Pro Arg Asp Ser Gly Leu Tyr Ala Cys Thr Ala Ser Arg Thr
            100                 105                 110

Val Asp Ser Glu Thr Trp Tyr Phe Met Val Asn Val Thr Asp Ala Ile
    115                 120                 125

Ser Ser Gly Asp Asp Glu Asp Asp Thr Asp Gly Ala Glu Asp Phe Val
130                 135                 140

Ser Glu Asn Ser Asn Asn Lys Arg Ala Pro Tyr Trp Thr Asn Thr Glu
145                 150                 155                 160

Lys Met Glu Lys Arg Leu His Ala Val Pro Ala Ala Asn Thr Val Lys
                165                 170                 175

Phe Arg Cys Pro Ala Gly Gly Asn Pro Met Pro Thr Met Arg Trp Leu
            180                 185                 190

Lys Asn Gly Lys Glu Phe Lys Gln Glu His Arg Ile Gly Gly Tyr Lys
        195                 200                 205

Val Arg Asn Gln His Trp Ser Leu Ile Met Glu Ser Val Val Pro Ser
    210                 215                 220

Asp Lys Gly Asn Tyr Thr Cys Val Val Glu Asn Glu Tyr Gly Ser Ile
225                 230                 235                 240

Asn His Thr Tyr His Leu Asp Val Val Glu Arg Ser Pro His Arg Pro
                245                 250                 255

Ile Leu Gln Ala Gly Leu Pro Ala Asn Ala Ser Thr Val Val Gly Gly
            260                 265                 270

Asp Val Glu Phe Val Cys Lys Val Tyr Ser Asp Ala Gln Pro His Ile
    275                 280                 285

Gln Trp Ile Lys His Val Glu Lys Asn Gly Ser Lys Tyr Gly Pro Asp
290                 295                 300

Gly Leu Pro Tyr Leu Lys Val Leu Lys Ala Ala Gly Val Asn Thr Thr
305                 310                 315                 320

Asp Lys Glu Ile Glu Val Leu Tyr Ile Arg Asn Val Thr Phe Glu Asp
                325                 330                 335

Ala Gly Glu Tyr Thr Cys Leu Ala Gly Asn Ser Ile Gly Ile Ser Phe
            340                 345                 350

His Ser Ala Trp Leu Thr Val Leu Pro Ala Pro Gly Arg Glu Lys Glu
    355                 360                 365

Ile Thr Ala Ser Pro Asp Tyr Leu Glu Ile Ala Ile Tyr Cys Ile Gly
        370                 375                 380
```

```
Val Phe Leu Ile Ala Cys Met Val Val Thr Val Ile Leu Cys Arg Met
385                 390                 395                 400

Lys Asn Thr Thr Lys Pro Asp Phe Ser Ser Gln Pro Ala Val His
            405                 410                 415

Lys Leu Thr Lys Arg Ile Pro Leu Arg Arg Gln Val Thr Val Ser Ala
                420                 425                 430

Glu Ser Ser Ser Ser Met Asn Ser Asn Thr Pro Leu Val Arg Ile Thr
            435                 440                 445

Thr Arg Leu Ser Ser Thr Ala Asp Thr Pro Met Leu Ala Gly Val Ser
450                 455                 460

Glu Tyr Glu Leu Pro Glu Asp Pro Lys Trp Glu Phe Pro Arg Asp Lys
465                 470                 475                 480

Leu Thr Leu Gly Lys Pro Leu Gly Glu Gly Cys Phe Gly Gln Val Val
                485                 490                 495

Met Ala Glu Ala Val Gly Ile Asp Lys Asp Lys Pro Lys Glu Ala Val
                500                 505                 510

Thr Val Ala Val Lys Met Leu Lys Asp Asp Ala Thr Glu Lys Asp Leu
            515                 520                 525

Ser Asp Leu Val Ser Glu Met Glu Met Met Lys Met Ile Gly Lys His
530                 535                 540

Lys Asn Ile Ile Asn Leu Leu Gly Ala Cys Thr Gln Asp Gly Pro Leu
545                 550                 555                 560

Tyr Val Ile Val Glu Tyr Ala Ser Lys Gly Asn Leu Arg Glu Tyr Leu
                565                 570                 575

Arg Ala Arg Arg Pro Pro Gly Met Glu Tyr Ser Tyr Asp Ile Asn Arg
            580                 585                 590

Val Pro Glu Glu Gln Met Thr Phe Lys Asp Leu Val Ser Cys Thr Tyr
            595                 600                 605

Gln Leu Ala Arg Gly Met Glu Tyr Leu Ala Ser Gln Lys Cys Ile His
            610                 615                 620

Arg Asp Leu Ala Ala Arg Asn Val Leu Val Thr Glu Asn Asn Val Met
625                 630                 635                 640

Lys Ile Ala Asp Phe Gly Leu Ala Arg Asp Ile Asn Asn Ile Asp Tyr
                645                 650                 655

Tyr Lys Lys Thr Thr Asn Gly Arg Leu Pro Val Lys Trp Met Ala Pro
            660                 665                 670

Glu Ala Leu Phe Asp Arg Val Tyr Thr His Gln Ser Asp Val Trp Ser
                675                 680                 685

Phe Gly Val Leu Met Trp Glu Ile Phe Thr Leu Gly Gly Ser Pro Tyr
690                 695                 700

Pro Gly Ile Pro Val Glu Glu Leu Phe Lys Leu Leu Lys Glu Gly His
705                 710                 715                 720

Arg Met Asp Lys Pro Ala Asn Cys Thr Asn Glu Leu Tyr Met Met Met
                725                 730                 735

Arg Asp Cys Trp His Ala Val Pro Ser Gln Arg Pro Thr Phe Lys Gln
                740                 745                 750

Leu Val Glu Asp Leu Asp Arg Ile Leu Thr Leu Thr Thr Asn Glu Glu
            755                 760                 765

Tyr Leu Asp Leu Ser Gln Pro Leu Glu Gln Tyr Ser Pro Ser Tyr Pro
            770                 775                 780

Asp Thr Arg Ser Ser Cys Ser Ser Gly Asp Asp Ser Val Phe Ser Pro
785                 790                 795                 800

Asp Pro Met Pro Tyr Glu Pro Cys Leu Pro Gln Tyr Pro His Ile Asn
```

-continued

```
                    805                 810                 815
Gly Ser Val Lys Thr
            820

<210> SEQ ID NO 4
<211> LENGTH: 704
<212> TYPE: PRT
<213> ORGANISM: Homo sapiens

<400> SEQUENCE: 4

Met Val Ser Trp Gly Arg Phe Ile Cys Leu Val Val Thr Met Ala
1               5                   10                  15

Thr Leu Ser Leu Ala Arg Pro Ser Phe Ser Leu Val Glu Asp Thr Thr
                20                  25                  30

Leu Glu Pro Glu Gly Ala Pro Tyr Trp Thr Asn Thr Glu Lys Met Glu
            35                  40                  45

Lys Arg Leu His Ala Val Pro Ala Ala Asn Thr Val Lys Phe Arg Cys
    50                  55                  60

Pro Ala Gly Gly Asn Pro Met Pro Thr Met Arg Trp Leu Lys Asn Gly
65              70                  75                  80

Lys Glu Phe Lys Gln Glu His Arg Ile Gly Gly Tyr Lys Val Arg Asn
                85                  90                  95

Gln His Trp Ser Leu Ile Met Glu Ser Val Val Pro Ser Asp Lys Gly
                100                 105                 110

Asn Tyr Thr Cys Val Val Glu Asn Glu Tyr Gly Ser Ile Asn His Thr
            115                 120                 125

Tyr His Leu Asp Val Val Glu Arg Ser Pro His Arg Pro Ile Leu Gln
    130                 135                 140

Ala Gly Leu Pro Ala Asn Ala Ser Thr Val Val Gly Gly Asp Val Glu
145                 150                 155                 160

Phe Val Cys Lys Val Tyr Ser Asp Ala Gln Pro His Ile Gln Trp Ile
                165                 170                 175

Lys His Val Glu Lys Asn Gly Ser Lys Tyr Gly Pro Asp Gly Leu Pro
            180                 185                 190

Tyr Leu Lys Val Leu Lys Ala Ala Gly Val Asn Thr Thr Asp Lys Glu
        195                 200                 205

Ile Glu Val Leu Tyr Ile Arg Asn Val Thr Phe Glu Asp Ala Gly Glu
    210                 215                 220

Tyr Thr Cys Leu Ala Gly Asn Ser Ile Gly Ile Ser Phe His Ser Ala
225                 230                 235                 240

Trp Leu Thr Val Leu Pro Ala Pro Gly Arg Glu Lys Glu Ile Thr Ala
                245                 250                 255

Ser Pro Asp Tyr Leu Glu Ile Ala Ile Tyr Cys Ile Gly Val Phe Leu
            260                 265                 270

Ile Ala Cys Met Val Val Thr Val Ile Leu Cys Arg Met Lys Asn Thr
        275                 280                 285

Thr Lys Lys Pro Asp Phe Ser Ser Gln Pro Ala Val His Lys Leu Thr
    290                 295                 300

Lys Arg Ile Pro Leu Arg Arg Gln Val Ser Ala Glu Ser Ser Ser Ser
305                 310                 315                 320

Met Asn Ser Asn Thr Pro Leu Val Arg Ile Thr Thr Arg Leu Ser Ser
                325                 330                 335

Thr Ala Asp Thr Pro Met Leu Ala Gly Val Ser Glu Tyr Glu Leu Pro
            340                 345                 350
```

```
Glu Asp Pro Lys Trp Glu Phe Pro Arg Asp Lys Leu Thr Leu Gly Lys
            355                 360                 365

Pro Leu Gly Glu Gly Cys Phe Gly Gln Val Val Met Ala Glu Ala Val
        370                 375                 380

Gly Ile Asp Lys Asp Lys Pro Lys Glu Ala Val Thr Val Ala Val Lys
385                 390                 395                 400

Met Leu Lys Asp Asp Ala Thr Glu Lys Asp Leu Ser Asp Leu Val Ser
                405                 410                 415

Glu Met Glu Met Met Lys Met Ile Gly Lys His Lys Asn Ile Ile Asn
            420                 425                 430

Leu Leu Gly Ala Cys Thr Gln Asp Gly Pro Leu Tyr Val Ile Val Glu
        435                 440                 445

Tyr Ala Ser Lys Gly Asn Leu Arg Glu Tyr Leu Arg Ala Arg Arg Pro
    450                 455                 460

Pro Gly Met Glu Tyr Ser Tyr Asp Ile Asn Arg Val Pro Glu Glu Gln
465                 470                 475                 480

Met Thr Phe Lys Asp Leu Val Ser Cys Thr Tyr Gln Leu Ala Arg Gly
                485                 490                 495

Met Glu Tyr Leu Ala Ser Gln Lys Cys Ile His Arg Asp Leu Ala Ala
            500                 505                 510

Arg Asn Val Leu Val Thr Glu Asn Asn Val Met Lys Ile Ala Asp Phe
        515                 520                 525

Gly Leu Ala Arg Asp Ile Asn Asn Ile Asp Tyr Tyr Lys Lys Thr Thr
    530                 535                 540

Asn Gly Arg Leu Pro Val Lys Trp Met Ala Pro Glu Ala Leu Phe Asp
545                 550                 555                 560

Arg Val Tyr Thr His Gln Ser Asp Val Trp Ser Phe Gly Val Leu Met
                565                 570                 575

Trp Glu Ile Phe Thr Leu Gly Gly Ser Pro Tyr Pro Gly Ile Pro Val
            580                 585                 590

Glu Glu Leu Phe Lys Leu Leu Lys Glu Gly His Arg Met Asp Lys Pro
        595                 600                 605

Ala Asn Cys Thr Asn Glu Leu Tyr Met Met Met Arg Asp Cys Trp His
    610                 615                 620

Ala Val Pro Ser Gln Arg Pro Thr Phe Lys Gln Leu Val Glu Asp Leu
625                 630                 635                 640

Asp Arg Ile Leu Thr Leu Thr Thr Asn Glu Glu Tyr Leu Asp Leu Ser
                645                 650                 655

Gln Pro Leu Glu Gln Tyr Ser Pro Ser Tyr Pro Asp Thr Arg Ser Ser
            660                 665                 670

Cys Ser Ser Gly Asp Asp Ser Val Phe Ser Pro Asp Pro Met Pro Tyr
        675                 680                 685

Glu Pro Cys Leu Pro Gln Tyr Pro His Ile Asn Gly Ser Val Lys Thr
    690                 695                 700

<210> SEQ ID NO 5
<211> LENGTH: 806
<212> TYPE: PRT
<213> ORGANISM: Homo sapiens

<400> SEQUENCE: 5

Met Gly Ala Pro Ala Cys Ala Leu Ala Leu Cys Val Ala Val Ala Ile
1               5                   10                  15

Val Ala Gly Ala Ser Ser Glu Ser Leu Gly Thr Glu Gln Arg Val Val
            20                  25                  30
```

```
Gly Arg Ala Ala Glu Val Pro Gly Pro Glu Pro Gly Gln Gln Glu Gln
         35                  40                  45

Leu Val Phe Gly Ser Gly Asp Ala Val Glu Leu Ser Cys Pro Pro Pro
     50                  55                  60

Gly Gly Gly Pro Met Gly Pro Thr Val Trp Val Lys Asp Gly Thr Gly
65                  70                  75                  80

Leu Val Pro Ser Glu Arg Val Leu Val Gly Pro Gln Arg Leu Gln Val
                 85                  90                  95

Leu Asn Ala Ser His Glu Asp Ser Gly Ala Tyr Ser Cys Arg Gln Arg
                100                 105                 110

Leu Thr Gln Arg Val Leu Cys His Phe Ser Val Arg Val Thr Asp Ala
            115                 120                 125

Pro Ser Ser Gly Asp Asp Glu Asp Gly Glu Asp Glu Ala Glu Asp Thr
        130                 135                 140

Gly Val Asp Thr Gly Ala Pro Tyr Trp Thr Arg Pro Glu Arg Met Asp
145                 150                 155                 160

Lys Lys Leu Leu Ala Val Pro Ala Ala Asn Thr Val Arg Phe Arg Cys
                165                 170                 175

Pro Ala Ala Gly Asn Pro Thr Pro Ser Ile Ser Trp Leu Lys Asn Gly
            180                 185                 190

Arg Glu Phe Arg Gly Glu His Arg Ile Gly Gly Ile Lys Leu Arg His
        195                 200                 205

Gln Gln Trp Ser Leu Val Met Glu Ser Val Val Pro Ser Asp Arg Gly
    210                 215                 220

Asn Tyr Thr Cys Val Val Glu Asn Lys Phe Gly Ser Ile Arg Gln Thr
225                 230                 235                 240

Tyr Thr Leu Asp Val Leu Glu Arg Ser Pro His Arg Pro Ile Leu Gln
                245                 250                 255

Ala Gly Leu Pro Ala Asn Gln Thr Ala Val Leu Gly Ser Asp Val Glu
            260                 265                 270

Phe His Cys Lys Val Tyr Ser Asp Ala Gln Pro His Ile Gln Trp Leu
        275                 280                 285

Lys His Val Glu Val Asn Gly Ser Lys Val Gly Pro Asp Gly Thr Pro
    290                 295                 300

Tyr Val Thr Val Leu Lys Thr Ala Gly Ala Asn Thr Thr Asp Lys Glu
305                 310                 315                 320

Leu Glu Val Leu Ser Leu His Asn Val Thr Phe Glu Asp Ala Gly Glu
                325                 330                 335

Tyr Thr Cys Leu Ala Gly Asn Ser Ile Gly Phe Ser His His Ser Ala
            340                 345                 350

Trp Leu Val Val Leu Pro Ala Glu Glu Glu Leu Val Glu Ala Asp Glu
        355                 360                 365

Ala Gly Ser Val Tyr Ala Gly Ile Leu Ser Tyr Gly Val Gly Phe Phe
    370                 375                 380

Leu Phe Ile Leu Val Val Ala Ala Val Thr Leu Cys Arg Leu Arg Ser
385                 390                 395                 400

Pro Pro Lys Lys Gly Leu Gly Ser Pro Thr Val His Lys Ile Ser Arg
                405                 410                 415

Phe Pro Leu Lys Arg Gln Val Ser Leu Glu Ser Asn Ala Ser Met Ser
            420                 425                 430

Ser Asn Thr Pro Leu Val Arg Ile Ala Arg Leu Ser Ser Gly Glu Gly
        435                 440                 445
```

```
Pro Thr Leu Ala Asn Val Ser Glu Leu Glu Leu Pro Ala Asp Pro Lys
    450                 455                 460

Trp Glu Leu Ser Arg Ala Arg Leu Thr Leu Gly Lys Pro Leu Gly Glu
465                 470                 475                 480

Gly Cys Phe Gly Gln Val Val Met Ala Glu Ala Ile Gly Ile Asp Lys
                485                 490                 495

Asp Arg Ala Ala Lys Pro Val Thr Val Ala Val Lys Met Leu Lys Asp
            500                 505                 510

Asp Ala Thr Asp Lys Asp Leu Ser Asp Leu Val Ser Glu Met Glu Met
        515                 520                 525

Met Lys Met Ile Gly Lys His Lys Asn Ile Ile Asn Leu Leu Gly Ala
530                 535                 540

Cys Thr Gln Gly Gly Pro Leu Tyr Val Leu Val Glu Tyr Ala Ala Lys
545                 550                 555                 560

Gly Asn Leu Arg Glu Phe Leu Arg Ala Arg Arg Pro Pro Gly Leu Asp
                565                 570                 575

Tyr Ser Phe Asp Thr Cys Lys Pro Pro Glu Glu Gln Leu Thr Phe Lys
            580                 585                 590

Asp Leu Val Ser Cys Ala Tyr Gln Val Ala Arg Gly Met Glu Tyr Leu
        595                 600                 605

Ala Ser Gln Lys Cys Ile His Arg Asp Leu Ala Ala Arg Asn Val Leu
    610                 615                 620

Val Thr Glu Asp Asn Val Met Lys Ile Ala Asp Phe Gly Leu Ala Arg
625                 630                 635                 640

Asp Val His Asn Leu Asp Tyr Tyr Lys Lys Thr Thr Asn Gly Arg Leu
                645                 650                 655

Pro Val Lys Trp Met Ala Pro Glu Ala Leu Phe Asp Arg Val Tyr Thr
            660                 665                 670

His Gln Ser Asp Val Trp Ser Phe Gly Val Leu Leu Trp Glu Ile Phe
        675                 680                 685

Thr Leu Gly Gly Ser Pro Tyr Pro Gly Ile Pro Val Glu Glu Leu Phe
    690                 695                 700

Lys Leu Leu Lys Glu Gly His Arg Met Asp Lys Pro Ala Asn Cys Thr
705                 710                 715                 720

His Asp Leu Tyr Met Ile Met Arg Glu Cys Trp His Ala Ala Pro Ser
                725                 730                 735

Gln Arg Pro Thr Phe Lys Gln Leu Val Glu Asp Leu Asp Arg Val Leu
            740                 745                 750

Thr Val Thr Ser Thr Asp Glu Tyr Leu Asp Leu Ser Ala Pro Phe Glu
        755                 760                 765

Gln Tyr Ser Pro Gly Gly Gln Asp Thr Pro Ser Ser Ser Ser Ser Gly
    770                 775                 780

Asp Asp Ser Val Phe Ala His Asp Leu Leu Pro Pro Ala Pro Pro Ser
785                 790                 795                 800

Ser Gly Gly Ser Arg Thr
                805

<210> SEQ ID NO 6
<211> LENGTH: 802
<212> TYPE: PRT
<213> ORGANISM: Homo sapiens

<400> SEQUENCE: 6

Met Arg Leu Leu Leu Ala Leu Leu Gly Val Leu Leu Ser Val Pro Gly
1               5                   10                  15
```

```
Pro Pro Val Leu Ser Leu Glu Ala Ser Glu Val Glu Leu Glu Pro
            20                  25                  30

Cys Leu Ala Pro Ser Leu Glu Gln Gln Glu Gln Leu Thr Val Ala
            35                  40                  45

Leu Gly Gln Pro Val Arg Leu Cys Gly Arg Ala Glu Arg Gly Gly
 50                  55                  60

His Trp Tyr Lys Glu Gly Ser Arg Leu Ala Pro Ala Gly Arg Val Arg
 65                  70                  75                  80

Gly Trp Arg Gly Arg Leu Glu Ile Ala Ser Phe Leu Pro Glu Asp Ala
                 85                  90                  95

Gly Arg Tyr Leu Cys Leu Ala Arg Gly Ser Met Ile Val Leu Gln Asn
             100                 105                 110

Leu Thr Leu Ile Thr Gly Asp Ser Leu Thr Ser Ser Asn Asp Asp Glu
         115                 120                 125

Asp Pro Lys Ser His Arg Asp Pro Ser Asn Arg His Ser Tyr Pro Gln
 130                 135                 140

Gln Ala Pro Tyr Trp Thr His Pro Gln Arg Met Glu Lys Lys Leu His
 145                 150                 155                 160

Ala Val Pro Ala Gly Asn Thr Val Lys Phe Arg Cys Pro Ala Ala Gly
                 165                 170                 175

Asn Pro Thr Pro Thr Ile Arg Trp Leu Lys Asp Gly Gln Ala Phe His
             180                 185                 190

Gly Glu Asn Arg Ile Gly Gly Ile Arg Leu Arg His Gln His Trp Ser
         195                 200                 205

Leu Val Met Glu Ser Val Val Pro Ser Asp Arg Gly Thr Tyr Thr Cys
     210                 215                 220

Leu Val Glu Asn Ala Val Gly Ser Ile Arg Tyr Asn Tyr Leu Leu Asp
225                 230                 235                 240

Val Leu Glu Arg Ser Pro His Arg Pro Ile Leu Gln Ala Gly Leu Pro
             245                 250                 255

Ala Asn Thr Thr Ala Val Val Gly Ser Asp Val Glu Leu Leu Cys Lys
         260                 265                 270

Val Tyr Ser Asp Ala Gln Pro His Ile Gln Trp Leu Lys His Ile Val
     275                 280                 285

Ile Asn Gly Ser Ser Phe Gly Ala Asp Gly Phe Pro Tyr Val Gln Val
 290                 295                 300

Leu Lys Thr Ala Asp Ile Asn Ser Ser Glu Val Glu Val Leu Tyr Leu
305                 310                 315                 320

Arg Asn Val Ser Ala Glu Asp Ala Gly Glu Tyr Thr Cys Leu Ala Gly
             325                 330                 335

Asn Ser Ile Gly Leu Ser Tyr Gln Ser Ala Trp Leu Thr Val Leu Pro
         340                 345                 350

Glu Glu Asp Pro Thr Trp Thr Ala Ala Ala Pro Glu Ala Arg Tyr Thr
     355                 360                 365

Asp Ile Ile Leu Tyr Ala Ser Gly Ser Leu Ala Leu Ala Val Leu Leu
 370                 375                 380

Leu Leu Ala Gly Leu Tyr Arg Gly Gln Ala Leu His Gly Arg His Pro
385                 390                 395                 400

Arg Pro Pro Ala Thr Val Gln Lys Leu Ser Arg Phe Pro Leu Ala Arg
             405                 410                 415

Gln Phe Ser Leu Glu Ser Gly Ser Ser Gly Lys Ser Ser Ser Ser Leu
         420                 425                 430
```

```
Val Arg Gly Val Arg Leu Ser Ser Gly Pro Ala Leu Leu Ala Gly
            435                 440                 445

Leu Val Ser Leu Asp Leu Pro Leu Asp Pro Leu Trp Glu Phe Pro Arg
450                 455                 460

Asp Arg Leu Val Leu Gly Lys Pro Leu Gly Glu Gly Cys Phe Gly Gln
465                 470                 475                 480

Val Val Arg Ala Glu Ala Phe Gly Met Asp Pro Ala Arg Pro Asp Gln
                485                 490                 495

Ala Ser Thr Val Ala Val Lys Met Leu Lys Asp Asn Ala Ser Asp Lys
                500                 505                 510

Asp Leu Ala Asp Leu Val Ser Glu Met Glu Val Met Lys Leu Ile Gly
                515                 520                 525

Arg His Lys Asn Ile Ile Asn Leu Leu Gly Val Cys Thr Gln Glu Gly
530                 535                 540

Pro Leu Tyr Val Ile Val Glu Cys Ala Ala Lys Gly Asn Leu Arg Glu
545                 550                 555                 560

Phe Leu Arg Ala Arg Arg Pro Pro Gly Pro Asp Leu Ser Pro Asp Gly
                565                 570                 575

Pro Arg Ser Ser Glu Gly Pro Leu Ser Phe Pro Val Leu Val Ser Cys
                580                 585                 590

Ala Tyr Gln Val Ala Arg Gly Met Gln Tyr Leu Glu Ser Arg Lys Cys
                595                 600                 605

Ile His Arg Asp Leu Ala Ala Arg Asn Val Leu Val Thr Glu Asp Asn
            610                 615                 620

Val Met Lys Ile Ala Asp Phe Gly Leu Ala Arg Gly Val His His Ile
625                 630                 635                 640

Asp Tyr Tyr Lys Lys Thr Ser Asn Gly Arg Leu Pro Val Lys Trp Met
                645                 650                 655

Ala Pro Glu Ala Leu Phe Asp Arg Val Tyr Thr His Gln Ser Asp Val
                660                 665                 670

Trp Ser Phe Gly Ile Leu Leu Trp Glu Ile Phe Thr Leu Gly Gly Ser
            675                 680                 685

Pro Tyr Pro Gly Ile Pro Val Glu Glu Leu Phe Ser Leu Leu Arg Glu
690                 695                 700

Gly His Arg Met Asp Arg Pro Pro His Cys Pro Pro Glu Leu Tyr Gly
705                 710                 715                 720

Leu Met Arg Glu Cys Trp His Ala Ala Pro Ser Gln Arg Pro Thr Phe
                725                 730                 735

Lys Gln Leu Val Glu Ala Leu Asp Lys Val Leu Leu Ala Val Ser Glu
                740                 745                 750

Glu Tyr Leu Asp Leu Arg Leu Thr Phe Gly Pro Tyr Ser Pro Ser Gly
                755                 760                 765

Gly Asp Ala Ser Ser Thr Cys Ser Ser Ser Asp Ser Val Phe Ser His
            770                 775                 780

Asp Pro Leu Pro Leu Gly Ser Ser Ser Phe Pro Phe Gly Ser Gly Val
785                 790                 795                 800

Gln Thr

<210> SEQ ID NO 7
<211> LENGTH: 760
<212> TYPE: PRT
<213> ORGANISM: Homo sapiens

<400> SEQUENCE: 7
```

```
Met Lys Glu Ala Ala Leu Ile Cys Leu Ala Pro Ser Val Pro Pro Ile
1               5                   10                  15

Leu Thr Val Lys Ser Trp Asp Thr Met Gln Leu Arg Ala Ala Arg Ser
            20                  25                  30

Arg Cys Thr Asn Leu Leu Ala Ala Ser Tyr Ile Glu Asn Gln Gln His
        35                  40                  45

Leu Gln His Leu Glu Leu Arg Asp Leu Arg Gly Leu Gly Glu Leu Arg
    50                  55                  60

Asn Leu Thr Ile Val Lys Ser Gly Leu Arg Phe Val Ala Pro Asp Ala
65                  70                  75                  80

Phe His Phe Thr Pro Arg Leu Ser Arg Leu Asn Leu Ser Phe Asn Ala
                85                  90                  95

Leu Glu Ser Leu Ser Trp Lys Thr Val Gln Gly Leu Ser Leu Gln Glu
                100                 105                 110

Leu Val Leu Ser Gly Asn Pro Leu His Cys Ser Cys Ala Leu Arg Trp
            115                 120                 125

Leu Gln Arg Trp Glu Glu Glu Gly Leu Gly Gly Val Pro Glu Gln Lys
    130                 135                 140

Leu Gln Cys His Gly Gln Gly Pro Leu Ala His Met Pro Asn Ala Ser
145                 150                 155                 160

Cys Gly Val Pro Thr Leu Lys Val Gln Val Pro Asn Ala Ser Val Asp
                165                 170                 175

Val Gly Asp Asp Val Leu Leu Arg Cys Gln Val Glu Gly Arg Gly Leu
            180                 185                 190

Glu Gln Ala Gly Trp Ile Leu Thr Glu Leu Glu Gln Ser Ala Thr Val
    195                 200                 205

Met Lys Ser Gly Gly Leu Pro Ser Leu Gly Leu Thr Leu Ala Asn Val
    210                 215                 220

Thr Ser Asp Leu Asn Arg Lys Asn Val Thr Cys Trp Ala Glu Asn Asp
225                 230                 235                 240

Val Gly Arg Ala Glu Val Ser Val Gln Val Asn Val Ser Phe Pro Ala
                245                 250                 255

Ser Val Gln Leu His Thr Ala Val Glu Met His His Trp Cys Ile Pro
                260                 265                 270

Phe Ser Val Asp Gly Gln Pro Ala Pro Ser Leu Arg Trp Leu Phe Asn
    275                 280                 285

Gly Ser Val Leu Asn Glu Thr Ser Phe Ile Phe Thr Glu Phe Leu Glu
    290                 295                 300

Pro Ala Ala Asn Glu Thr Val Arg His Gly Cys Leu Arg Leu Asn Gln
305                 310                 315                 320

Pro Thr His Val Asn Asn Gly Asn Tyr Thr Leu Leu Ala Ala Asn Pro
                325                 330                 335

Phe Gly Gln Ala Ser Ala Ser Ile Met Ala Ala Phe Met Asp Asn Pro
                340                 345                 350

Phe Glu Phe Asn Pro Glu Asp Pro Ile Pro Asp Thr Asn Ser Thr Ser
                355                 360                 365

Gly Asp Pro Val Glu Lys Lys Asp Glu Thr Pro Phe Gly Val Ser Val
    370                 375                 380

Ala Val Gly Leu Ala Val Phe Ala Cys Leu Phe Leu Ser Thr Leu Leu
385                 390                 395                 400

Leu Val Leu Asn Lys Cys Gly Arg Arg Asn Lys Phe Gly Ile Asn Arg
                405                 410                 415

Pro Ala Val Leu Ala Pro Glu Asp Gly Leu Ala Met Ser Leu His Phe
```

```
                420                 425                 430
Met Thr Leu Gly Gly Ser Ser Leu Ser Pro Thr Glu Gly Lys Gly Ser
            435                 440                 445

Gly Leu Gln Gly His Ile Ile Glu Asn Pro Gln Tyr Phe Ser Asp Ala
        450                 455                 460

Cys Val His His Ile Lys Arg Arg Asp Ile Val Leu Lys Trp Glu Leu
465                 470                 475                 480

Gly Glu Gly Ala Phe Gly Lys Val Phe Leu Ala Glu Cys His Asn Leu
                485                 490                 495

Leu Pro Glu Gln Asp Lys Met Leu Val Ala Val Lys Ala Leu Lys Glu
            500                 505                 510

Ala Ser Glu Ser Ala Arg Gln Asp Phe Gln Arg Glu Ala Glu Leu Leu
        515                 520                 525

Thr Met Leu Gln His Gln His Ile Val Arg Phe Phe Gly Val Cys Thr
            530                 535                 540

Glu Gly Arg Pro Leu Leu Met Val Phe Glu Tyr Met Arg His Gly Asp
545                 550                 555                 560

Leu Asn Arg Phe Leu Arg Ser His Gly Pro Asp Ala Lys Leu Leu Ala
                565                 570                 575

Gly Gly Glu Asp Val Ala Pro Gly Pro Leu Gly Leu Gly Gln Leu Leu
            580                 585                 590

Ala Val Ala Ser Gln Val Ala Ala Gly Met Val Tyr Leu Ala Gly Leu
        595                 600                 605

His Phe Val His Arg Asp Leu Ala Thr Arg Asn Cys Leu Val Gly Gln
            610                 615                 620

Gly Leu Val Val Lys Ile Gly Asp Phe Gly Met Ser Arg Asp Ile Tyr
625                 630                 635                 640

Ser Thr Asp Tyr Tyr Arg Val Gly Gly Arg Thr Met Leu Pro Ile Arg
                645                 650                 655

Trp Met Pro Pro Glu Ser Ile Leu Tyr Arg Lys Phe Thr Thr Glu Ser
            660                 665                 670

Asp Val Trp Ser Phe Gly Val Val Leu Trp Glu Ile Phe Thr Tyr Gly
        675                 680                 685

Lys Gln Pro Trp Tyr Gln Leu Ser Asn Thr Glu Ala Ile Asp Cys Ile
            690                 695                 700

Thr Gln Gly Arg Glu Leu Glu Arg Pro Arg Ala Cys Pro Pro Glu Val
705                 710                 715                 720

Tyr Ala Ile Met Arg Gly Cys Trp Gln Arg Glu Pro Gln Gln Arg His
                725                 730                 735

Ser Ile Lys Asp Val His Ala Arg Leu Gln Ala Leu Ala Gln Ala Pro
            740                 745                 750

Pro Val Tyr Leu Asp Val Leu Gly
        755                 760

<210> SEQ ID NO 8
<211> LENGTH: 477
<212> TYPE: PRT
<213> ORGANISM: Homo sapiens

<400> SEQUENCE: 8

Met Ser Ser Trp Ile Arg Trp His Gly Pro Ala Met Ala Arg Leu Trp
1               5                   10                  15

Gly Phe Cys Trp Leu Val Val Gly Phe Trp Arg Ala Ala Phe Ala Cys
            20                  25                  30
```

```
Pro Thr Ser Cys Lys Cys Ser Ala Ser Arg Ile Trp Cys Ser Asp Pro
            35                  40                  45

Ser Pro Gly Ile Val Ala Phe Pro Arg Leu Glu Pro Asn Ser Val Asp
 50                  55                  60

Pro Glu Asn Ile Thr Glu Ile Phe Ile Ala Asn Gln Lys Arg Leu Glu
 65                  70                  75                  80

Ile Ile Asn Glu Asp Asp Val Glu Ala Tyr Val Gly Leu Arg Asn Leu
                 85                  90                  95

Thr Ile Val Asp Ser Gly Leu Lys Phe Val Ala His Lys Ala Phe Leu
            100                 105                 110

Lys Asn Ser Asn Leu Gln His Ile Asn Phe Thr Arg Asn Lys Leu Thr
            115                 120                 125

Ser Leu Ser Arg Lys His Phe Arg His Leu Asp Leu Ser Glu Leu Ile
130                 135                 140

Leu Val Gly Asn Pro Phe Thr Cys Ser Cys Asp Ile Met Trp Ile Lys
145                 150                 155                 160

Thr Leu Gln Glu Ala Lys Ser Ser Pro Asp Thr Gln Asp Leu Tyr Cys
                165                 170                 175

Leu Asn Glu Ser Ser Lys Asn Ile Pro Leu Ala Asn Leu Gln Ile Pro
            180                 185                 190

Asn Cys Gly Leu Pro Ser Ala Asn Leu Ala Ala Pro Asn Leu Thr Val
            195                 200                 205

Glu Glu Gly Lys Ser Ile Thr Leu Ser Cys Ser Val Ala Gly Asp Pro
            210                 215                 220

Val Pro Asn Met Tyr Trp Asp Val Gly Asn Leu Val Ser Lys His Met
225                 230                 235                 240

Asn Glu Thr Ser His Thr Gln Gly Ser Leu Arg Ile Thr Asn Ile Ser
                245                 250                 255

Ser Asp Asp Ser Gly Lys Gln Ile Ser Cys Val Ala Glu Asn Leu Val
            260                 265                 270

Gly Glu Asp Gln Asp Ser Val Asn Leu Thr Val His Phe Ala Pro Thr
            275                 280                 285

Ile Thr Phe Leu Glu Ser Pro Thr Ser Asp His His Trp Cys Ile Pro
290                 295                 300

Phe Thr Val Lys Gly Asn Pro Lys Pro Ala Leu Gln Trp Phe Tyr Asn
305                 310                 315                 320

Gly Ala Ile Leu Asn Glu Ser Lys Tyr Ile Cys Thr Lys Ile His Val
                325                 330                 335

Thr Asn His Thr Glu Tyr His Gly Cys Leu Gln Leu Asp Asn Pro Thr
            340                 345                 350

His Met Asn Asn Gly Asp Tyr Thr Leu Ile Ala Lys Asn Glu Tyr Gly
            355                 360                 365

Lys Asp Glu Lys Gln Ile Ser Ala His Phe Met Gly Trp Pro Gly Ile
            370                 375                 380

Asp Asp Gly Ala Asn Pro Asn Tyr Pro Asp Val Ile Tyr Glu Asp Tyr
385                 390                 395                 400

Gly Thr Ala Ala Asn Asp Ile Gly Asp Thr Thr Asn Arg Ser Asn Glu
                405                 410                 415

Ile Pro Ser Thr Asp Val Thr Asp Lys Thr Gly Arg Glu His Leu Ser
            420                 425                 430

Val Tyr Ala Val Val Val Ile Ala Ser Val Val Gly Phe Cys Leu Leu
            435                 440                 445

Val Met Leu Phe Leu Leu Lys Leu Ala Arg His Ser Lys Phe Gly Met
```

```
                    450                 455                 460
Lys Gly Phe Val Leu Phe His Lys Ile Pro Leu Asp Gly
465                 470                 475

<210> SEQ ID NO 9
<211> LENGTH: 612
<212> TYPE: PRT
<213> ORGANISM: Homo sapiens

<400> SEQUENCE: 9

Met Asp Val Ser Leu Cys Pro Ala Lys Cys Ser Phe Trp Arg Ile Phe
1               5                   10                  15

Leu Leu Gly Ser Val Trp Leu Asp Tyr Val Gly Ser Val Leu Ala Cys
            20                  25                  30

Pro Ala Asn Cys Val Cys Ser Lys Thr Glu Ile Asn Cys Arg Arg Pro
        35                  40                  45

Asp Asp Gly Asn Leu Phe Pro Leu Leu Glu Gly Gln Asp Ser Gly Asn
    50                  55                  60

Ser Asn Gly Asn Ala Ser Ile Asn Ile Thr Asp Ile Ser Arg Asn Ile
65                  70                  75                  80

Thr Ser Ile His Ile Glu Asn Trp Arg Ser Leu His Thr Leu Asn Ala
                85                  90                  95

Val Asp Met Glu Leu Tyr Thr Gly Leu Gln Lys Leu Thr Ile Lys Asn
            100                 105                 110

Ser Gly Leu Arg Ser Ile Gln Pro Arg Ala Phe Ala Lys Asn Pro His
        115                 120                 125

Leu Arg Tyr Ile Asn Leu Ser Ser Asn Arg Leu Thr Thr Leu Ser Trp
    130                 135                 140

Gln Leu Phe Gln Thr Leu Ser Leu Arg Glu Leu Gln Leu Glu Gln Asn
145                 150                 155                 160

Phe Phe Asn Cys Ser Cys Asp Ile Arg Trp Met Gln Leu Trp Gln Glu
                165                 170                 175

Gln Gly Glu Ala Lys Leu Asn Ser Gln Asn Leu Tyr Cys Ile Asn Ala
            180                 185                 190

Asp Gly Ser Gln Leu Pro Leu Phe Arg Met Asn Ile Ser Gln Cys Asp
        195                 200                 205

Leu Pro Glu Ile Ser Val Ser His Val Asn Leu Thr Val Arg Glu Gly
    210                 215                 220

Asp Asn Ala Val Ile Thr Cys Asn Gly Ser Gly Ser Pro Leu Pro Asp
225                 230                 235                 240

Val Asp Trp Ile Val Thr Gly Leu Gln Ser Ile Asn Thr His Gln Thr
                245                 250                 255

Asn Leu Asn Trp Thr Asn Val His Ala Ile Asn Leu Thr Leu Val Asn
            260                 265                 270

Val Thr Ser Glu Asp Asn Gly Phe Thr Leu Thr Cys Ile Ala Glu Asn
        275                 280                 285

Val Val Gly Met Ser Asn Ala Ser Val Ala Leu Thr Val Tyr Tyr Pro
    290                 295                 300

Pro Arg Val Val Ser Leu Glu Glu Pro Glu Leu Arg Leu Glu His Cys
305                 310                 315                 320

Ile Glu Phe Val Val Arg Gly Asn Pro Pro Thr Leu His Trp Leu
                325                 330                 335

His Asn Gly Gln Pro Leu Arg Glu Ser Lys Ile Ile His Val Glu Tyr
            340                 345                 350
```

```
Tyr Gln Glu Gly Glu Ile Ser Glu Gly Cys Leu Leu Phe Asn Lys Pro
            355                 360                 365

Thr His Tyr Asn Asn Gly Asn Tyr Thr Leu Ile Ala Lys Asn Pro Leu
    370                 375                 380

Gly Thr Ala Asn Gln Thr Ile Asn Gly His Phe Leu Lys Glu Pro Phe
385                 390                 395                 400

Pro Glu Ser Thr Asp Asn Phe Ile Leu Phe Asp Glu Val Ser Pro Thr
                405                 410                 415

Pro Pro Ile Thr Val Thr His Lys Pro Glu Asp Thr Phe Gly Val
            420                 425                 430

Ser Ile Ala Val Gly Leu Ala Ala Phe Ala Cys Val Leu Leu Val Val
            435                 440                 445

Leu Phe Val Met Ile Asn Lys Tyr Gly Arg Arg Ser Lys Phe Gly Met
    450                 455                 460

Lys Gly Pro Val Ala Val Ile Ser Gly Glu Glu Asp Ser Ala Ser Pro
465                 470                 475                 480

Leu His His Ile Asn His Gly Ile Thr Thr Pro Ser Ser Leu Asp Ala
                485                 490                 495

Gly Pro Asp Thr Val Val Ile Gly Met Thr Arg Ile Pro Val Ile Glu
            500                 505                 510

Asn Pro Gln Tyr Phe Arg Gln Gly His Asn Cys His Lys Pro Asp Thr
        515                 520                 525

Trp Val Phe Ser Asn Ile Asp Asn His Gly Ile Leu Asn Leu Lys Asp
    530                 535                 540

Asn Arg Asp His Leu Val Pro Ser Thr His Tyr Ile Tyr Glu Glu Pro
545                 550                 555                 560

Glu Val Gln Ser Gly Glu Val Ser Tyr Pro Arg Ser His Gly Phe Arg
                565                 570                 575

Glu Ile Met Leu Asn Pro Ile Ser Leu Pro Gly His Ser Lys Pro Leu
            580                 585                 590

Asn His Gly Ile Tyr Val Glu Asp Val Asn Val Tyr Phe Ser Lys Gly
        595                 600                 605

Arg His Gly Phe
    610

<210> SEQ ID NO 10
<211> LENGTH: 4797
<212> TYPE: DNA
<213> ORGANISM: Homo sapiens

<400> SEQUENCE: 10
cgcaactttg cctcccaggg aacaaacatc ctccttctaa gtggtagatg tgggtgagct      60
gaccctgctg gagtctgtcc cctgggctac cctctgcttc ccccattgt gagtggtccg      120 tgaagcacag cgttgaccag acctaaacct gtttgctccc aggacaaggt ggagcagaca     180
cctcgcagtc aacaagaccc ggcaggacca ggactcccg cacagtctga ccgacttgcg      240
aatcaccagg aggatgatgt ggacctggaa gccctggtga cgatatgaa tgcatccctg      300 gagagcctgt actcggcctg cagcatgcag tcagacacgg tgcccctcct gcagaatggc     360
cagcatgccc gcagccagcc tcgggcttca ggccctcctc ggtccatcca gccacaggtg     420
tccccgaggc agagggtgca gcgctcccag cctgtgcaca tcctcgctgt caggcgcctt     480
caggaggaag accagcagtt tagaacctca tctctgccgg ccatccccaa tccttttcct     540
gaactctgtg gccctgggag ccccccctgt ctcacgccgg gttctttacc tccgagccag     600
```

```
gccgccgcaa agcaggatgt taaagtcttt agtgaagatg ggacaagcaa agtggtggag    660
attctagcag acatgacagc cagagacctg tgccaattgc tggtttacaa aagtcactgt    720
gtggatgaca acagctggac actagtggag caccaccgc acctaggatt agagaggtgc     780
ttggaagacc atgagctggt ggtccaggtg gagagtacca tggccagtga gagtaaattt    840
ctattcagga agaattacgc aaaatacgag ttctttaaaa atcccatgaa tttcttccca    900
gaacagatgg ttacttggtg ccagcagtca aatggcagtc aaacccagct tttgcagaat    960
tttctgaact ccagtagttg tcctgaaatt caagggtttt tgcatgtgaa agagctggga    1020
aagaaatcat ggaaaaagct gtatgtgtgt ttgcggagat ctggcccttta ttgctccacc   1080 aagggaactt caaggaacc cagacacctg cagctgctgg ccgacctgga ggacagcaac     1140
atcttctccc tgatcgctgg caggaagcag tacaacgccc ctacagacca cgggctctgc    1200
ataaagccaa acaaagtcag gaatgaaact aaagagctga ggttgctctg tgcagaggac    1260
gagcaaacca ggacgtgctg gatgacagct tcagactcc tcaagtatgg aatgctcctt     1320
taccagaatt accgaatccc tcagcagagg aaggccttgc tgtccccgtt ctcgacgcca    1380
gtgcgcagtg tctccgagaa ctccctcgtg gcaatggatt tttctgggca aacaggacgc    1440
gtgatagaga atccggcgga ggcccagagc gcagccctgg aggagggcca cgcctggagg    1500
aagcgaagca cacggatgaa catcctaggt agccaaagtc ccctccaccc ttctacccta    1560
agtacagtga ttcacaggac acagcactgg tttcacggga ggatctccag ggaggaatcc    1620
cacaggatca ttaaacagca agggctcgtg gatgggcttt ttctcctccg tgacagccag    1680
agtaatccaa aggcatttgt actcacactg tgtcatcacc agaaaattaa aaatttccag    1740 atcttaccttt gcgaggacga cgggcagacg ttcttcagcc tagatgacgg gaacaccaaa   1800
ttctctgacc tgatccagct ggttgacttt taccagctga acaaaggagt cctgccttgc    1860
aaactcaagc accactgcat ccgagtggcc ttatgaccgc agatgtcctc tcggctgaag    1920
actggaggaa gtgaacactg gagtgaagaa gcggtctgtg cgttggtgaa gaacacacat    1980
cgattctgca cctggggacc cagagcgaga tgggtttgtt cggtgccagc cgaccaagat    2040
tgactagttt gttggactta acgacgatt tgctgctgtg aacccagcag ggtcgcctcc     2100
ctctgcgtcg gccaaattgg ggagggcatg aagatccag cggaaagttg aaaataaact     2160
ggaatgatca tcttggcttg ggccgcttag gaacaagaac cggagagaag tgattggaaa    2220
tgaactcttg ccctggaata atcttgacaa ttaaaactga tatgtttact ttttttgtat    2280
tgatcacttt tttgcactcc ttctttgttt tcaatattgt attcagccta ttgtaggagg    2340
gggatgtggc gtttcaactc atataataca gaaagagttt tgaatgggca gatttcaaac    2400
tgaatatggg tccccaaatg ttcccagagg gtcctccaca ccctctgccg actaccacgg    2460
tgtggattca gctcccaaat gacaaaccca gcccttccca gtatacttga aaagctttct    2520
tgttaaaata aaaggtgtca ctgtggtagg catttggcat attttgtgga ctcagtcaag    2580
caaccacagt ctgttaatca tttctctatg ctcagatgtc agatcctctt gttattagtg    2640
tgtcttgttc tgcacagtgc aggagacttt attcctttgg aaaattcact gttccacaaa    2700
cagcaggctg aatggcctcg cctctagatt gacgtgggcc agcctccttg agacacacct    2760
ggcacccgtc atcggccagc ggtggatgct gcataatcca cctgggtact tcagccttgc    2820
gtttccacag ccttcagcct gttctagaac gatcactgcc ttaccctgc tgctgcagtg     2880 gtgtgagtcg tttcacggct gatgtccctc gggggattaa aggatctaaa gagaaaatgg    2940
cacctggttg tcttcgtgct gtgtctcatg ggtttccata gtgataaaga caaggaaacg    3000
```

-continued

```
ctgcagggc cacaggcaca ggctgatatt taaagatctt tgcttgcagc cctccgtcct   3060
gctgaaaacc cccataagcc agtgaacaca gagcagctag aggctcctcc tctgctggct   3120
tagggtcaga agtacctcac agtggttgtg gacatggaag agttttgtca acacaacact   3180
ttgtccccgc tccgggagat gagtcagatg gtggcttgag ttgtcacttg gtcccctccg   3240
cccctcgggt ggccccctttt gccacgtccc cttagcttag tgatcaggtg tgagagtggc   3300
catttcctta cctttgatcc ctgtaaagca gaaaggactc ctttgacagg cgacaaacta   3360
ctgtggtgag cagaatgatt tccttttttca agacaacacc tgcctggctt ctattaatgt   3420
gtgctggcca tgatattgcc ccaaatccgc cccactgaag tgttccctaa ggaacagcat   3480
ttctctgctc ctcagtcaac ccccgtagcc tagagcagtg tcacaagctt cagtaaggcc   3540
agtcagctgg aagtcagtct accgtatagt aacactgtat ttcagtctac agaccacact   3600
ctagttgttt tccatgaaag gtatacaaat gaagaatttt ctagcaaaac atgttttttaa   3660
ccatcagtgc tcaattgcat tttcttcctt tcgcagccag tcagtctttc aaactattga   3720
cagtaagata attctcacgt tcacacctgg tggcaggctt cactgtaggg acggacattg   3780
cagttacacc acgattcctt cctcttcact ggctcgaggt aaaccccttt caaggaaaaa   3840
caactctagg atttcttttt tctgtgtacg tagaccagtc ccatcagtgt ataatctctc   3900
tctcacacgc ctctctccaa tagacagctt gtatttgcag tatttcatat ttataaatat   3960
gcgtttattt aaaaggagaa caaaagcttg actctgattc acagttttgt atgtagctgg   4020
tttgacgtag tcttttgtat tttccctgcc gaagtgaatt gttggagaat gtaaaccgcc   4080
tccacgtggc ggcagacttc ctaaggcccc agctcgctgg cctcgcgctg ggcggctggg   4140
aattccacct gagaacaagt cccgcaaacc ggggacggaa ggacatttga cttttatttt   4200
tgtatttaat tgacatgaat gtaaagggga cagctcaggg ttgttttgga gcctgttgac   4260
tttgtatctc tgcctgtgat tttctttttct aaatgaaact ccatgtagca accaggacga   4320
agttgagaag gaaaacgcca aatgctttgg ttattagagt ttaataggta agctctgtta   4380
cactaggtgt tagagttcca gaatgttctt ttgtttgcta aaccttgaag aaacatgtgc   4440
ctcagcctag atgttttgtc ttctcttttc tgcacttaat acctgacagt atgaccgatc   4500
tctgcgcctt tctgggggcg ggcaagctgc cggtagattt gtgatgtcac agtgcaaact   4560
gcagtgactg taaattggcc tggcgtgtat aaacgttttc agggaatgca gaaggtatta   4620
atgaagagac aaaacccttta ttccatgtgc tttgcttcat tctgtacata gctctttggc   4680
tcgtgaacct aattgtaaac tttcaggtat ttttgtacaa ataagggact gatgttctgt   4740
ttcttgtaat tagaaataaa cattaataca gtgttcttca aaaaaaaaa aaaaaaa      4797
```

<210> SEQ ID NO 11
<211> LENGTH: 410
<212> TYPE: PRT
<213> ORGANISM: Homo sapiens

<400> SEQUENCE: 11

```
Arg Leu Arg Ser Pro Pro Lys Lys Gly Leu Gly Ser Pro Thr Val His
1               5                   10                  15

Lys Ile Ser Arg Phe Pro Leu Lys Arg Gln Val Ser Leu Glu Ser Asn
            20                  25                  30

Ala Ser Met Ser Ser Asn Thr Pro Leu Val Arg Ile Ala Arg Leu Ser
        35                  40                  45

Ser Gly Glu Gly Pro Thr Leu Ala Asn Val Ser Glu Leu Glu Leu Pro
```

```
                50                  55                  60
Ala Asp Pro Lys Trp Glu Leu Ser Arg Ala Arg Leu Thr Leu Gly Lys
 65                  70                  75                  80

Pro Leu Gly Glu Gly Cys Phe Gly Gln Val Val Met Ala Glu Ala Ile
                 85                  90                  95

Gly Ile Asp Lys Asp Arg Ala Ala Lys Pro Val Thr Val Ala Val Lys
            100                 105                 110

Met Leu Lys Asp Asp Ala Thr Asp Lys Asp Leu Ser Asp Leu Val Ser
        115                 120                 125

Glu Met Glu Met Met Lys Met Ile Gly Lys His Lys Asn Ile Ile Asn
    130                 135                 140

Leu Leu Gly Ala Cys Thr Gln Gly Gly Pro Leu Tyr Val Leu Val Glu
145                 150                 155                 160

Tyr Ala Ala Lys Gly Asn Leu Arg Glu Phe Leu Arg Ala Arg Arg Pro
                165                 170                 175

Pro Gly Leu Asp Tyr Ser Phe Asp Thr Cys Lys Pro Pro Glu Glu Gln
            180                 185                 190

Leu Thr Phe Lys Asp Leu Val Ser Cys Ala Tyr Gln Val Ala Arg Gly
        195                 200                 205

Met Glu Tyr Leu Ala Ser Gln Lys Cys Ile His Arg Asp Leu Ala Ala
    210                 215                 220

Arg Asn Val Leu Val Thr Glu Asp Asn Val Met Lys Ile Ala Asp Phe
225                 230                 235                 240

Gly Leu Ala Arg Asp Val His Asn Leu Asp Tyr Tyr Lys Lys Thr Thr
                245                 250                 255

Asn Gly Arg Leu Pro Val Lys Trp Met Ala Pro Glu Ala Leu Phe Asp
            260                 265                 270

Arg Val Tyr Thr His Gln Ser Asp Val Trp Ser Phe Gly Val Leu Leu
        275                 280                 285

Trp Glu Ile Phe Thr Leu Gly Gly Ser Pro Tyr Pro Gly Ile Pro Val
    290                 295                 300

Glu Glu Leu Phe Lys Leu Leu Lys Glu Gly His Arg Met Asp Lys Pro
305                 310                 315                 320

Ala Asn Cys Thr His Asp Leu Tyr Met Ile Met Arg Glu Cys Trp His
                325                 330                 335

Ala Ala Pro Ser Gln Arg Pro Thr Phe Lys Gln Leu Val Glu Asp Leu
            340                 345                 350

Asp Arg Val Leu Thr Val Thr Ser Thr Asp Glu Tyr Leu Asp Leu Ser
        355                 360                 365

Ala Pro Phe Glu Gln Tyr Ser Pro Gly Gly Gln Asp Thr Pro Ser Ser
    370                 375                 380

Ser Ser Ser Gly Asp Asp Ser Val Phe Ala His Asp Leu Leu Pro Pro
385                 390                 395                 400

Ala Pro Pro Ser Ser Gly Gly Ser Arg Thr
                405                 410

<210> SEQ ID NO 12
<211> LENGTH: 258
<212> TYPE: PRT
<213> ORGANISM: Homo sapiens

<400> SEQUENCE: 12

Lys Lys Gly Leu Gly Ser Pro Thr Val His Lys Ile Ser Arg Phe Pro
 1               5                  10                  15
```

```
Leu Lys Arg Gln Val Ser Leu Glu Ser Asn Ala Ser Met Ser Ser Asn
             20                  25                  30

Thr Pro Leu Val Arg Ile Ala Arg Leu Ser Ser Gly Glu Gly Pro Thr
         35                  40                  45

Leu Ala Asn Val Ser Glu Leu Glu Leu Pro Ala Asp Pro Lys Trp Glu
 50                  55                  60

Leu Ser Arg Ala Arg Leu Thr Leu Gly Lys Pro Leu Gly Glu Gly Cys
 65                  70                  75                  80

Phe Gly Gln Val Val Met Ala Glu Ala Ile Gly Ile Asp Lys Asp Arg
                 85                  90                  95

Ala Ala Lys Pro Val Thr Val Val Lys Met Leu Lys Asp Asp Ala
             100                 105                 110

Thr Asp Lys Asp Leu Ser Asp Leu Val Ser Glu Met Glu Met Met Lys
             115                 120                 125

Met Ile Gly Lys His Lys Asn Ile Ile Asn Leu Leu Gly Ala Cys Thr
130                 135                 140

Gln Gly Gly Pro Leu Tyr Val Leu Val Glu Tyr Ala Ala Lys Gly Asn
145                 150                 155                 160

Leu Arg Glu Phe Leu Arg Ala Arg Arg Pro Pro Gly Leu Asp Tyr Ser
                165                 170                 175

Phe Asp Thr Cys Lys Pro Pro Glu Glu Gln Leu Thr Phe Lys Asp Leu
            180                 185                 190

Val Ser Cys Ala Tyr Gln Val Ala Arg Gly Met Glu Tyr Leu Ala Ser
        195                 200                 205

Gln Lys Cys Ile His Arg Asp Leu Ala Ala Arg Asn Val Leu Val Thr
210                 215                 220

Glu Asp Asn Val Met Lys Ile Ala Asp Phe Gly Leu Ala Arg Asp Val
225                 230                 235                 240

His Asn Leu Asp Tyr Tyr Lys Lys Thr Thr Asn Gly Arg Leu Pro Val
                245                 250                 255

Lys Trp

<210> SEQ ID NO 13
<211> LENGTH: 132
<212> TYPE: PRT
<213> ORGANISM: Homo sapiens

<400> SEQUENCE: 13

Met Ala Pro Glu Ala Leu Phe Asp Arg Val Tyr Thr His Gln Ser Asp
 1               5                  10                  15

Val Trp Ser Phe Gly Val Leu Leu Trp Glu Ile Phe Thr Leu Gly Gly
             20                  25                  30

Ser Pro Tyr Pro Gly Ile Pro Val Glu Glu Leu Phe Lys Leu Leu Lys
         35                  40                  45

Glu Gly His Arg Met Asp Lys Pro Ala Asn Cys Thr His Asp Leu Tyr
 50                  55                  60

Met Ile Met Arg Glu Cys Trp His Ala Ala Pro Ser Gln Arg Pro Thr
 65                  70                  75                  80

Phe Lys Gln Leu Val Glu Asp Leu Asp Arg Val Leu Thr Val Thr Ser
                 85                  90                  95

Thr Asp Glu Tyr Leu Asp Leu Ser Ala Pro Phe Glu Gln Tyr Ser Pro
            100                 105                 110

Gly Gly Gln Asp Thr Pro Ser Ser Ser Ser Gly Asp Asp Ser Val
        115                 120                 125
```

Phe Ala His Asp
    130

<210> SEQ ID NO 14
<211> LENGTH: 18
<212> TYPE: DNA
<213> ORGANISM: Artificial Sequence
<220> FEATURE:
<223> OTHER INFORMATION: primer

<400> SEQUENCE: 14
atgggcgccc ctgcctgc                                                 18

<210> SEQ ID NO 15
<211> LENGTH: 17
<212> TYPE: DNA
<213> ORGANISM: Artificial Sequence
<220> FEATURE:
<223> OTHER INFORMATION: primer

<400> SEQUENCE: 15
cgtccgcgag cccccac                                                  17

<210> SEQ ID NO 16
<211> LENGTH: 21
<212> TYPE: DNA
<213> ORGANISM: Artificial Sequence
<220> FEATURE:
<223> OTHER INFORMATION: primer

<400> SEQUENCE: 16
atgaagaaag gcctgggctc c                                             21

<210> SEQ ID NO 17
<211> LENGTH: 17
<212> TYPE: DNA
<213> ORGANISM: Artificial Sequence
<220> FEATURE:
<223> OTHER INFORMATION: primer

<400> SEQUENCE: 17
cgtccgcgag cccccac                                                  17

<210> SEQ ID NO 18
<211> LENGTH: 21
<212> TYPE: DNA
<213> ORGANISM: Artificial Sequence
<220> FEATURE:
<223> OTHER INFORMATION: primer

<400> SEQUENCE: 18
atgaagaaag gcctgggctc c                                             21

<210> SEQ ID NO 19
<211> LENGTH: 17
<212> TYPE: DNA
<213> ORGANISM: Artificial Sequence
<220> FEATURE:
<223> OTHER INFORMATION: primer

<400> SEQUENCE: 19
ccacttcacg ggcagcc                                                  17

<210> SEQ ID NO 20
<211> LENGTH: 18
<212> TYPE: DNA

```
<213> ORGANISM: Artificial Sequence
<220> FEATURE:
<223> OTHER INFORMATION: primer

<400> SEQUENCE: 20
atggcgcctg aggccttg                                                    18

<210> SEQ ID NO 21
<211> LENGTH: 17
<212> TYPE: DNA
<213> ORGANISM: Artificial Sequence
<220> FEATURE:
<223> OTHER INFORMATION: primer

<400> SEQUENCE: 21
cgtccgcgag cccccac                                                     17
```

FIBROBLAST GROWTH FACTOR RECEPTORS AS DIAGNOSTIC MARKERS OF ACQUIRED SENSORY NEURONOPATHIES

FIELD OF THE INVENTION

The present invention relates to the diagnosis of acquired sensory neuronopathies (SNN), and to the treatment of these disorders.

BACKGROUND

Acquired sensory neuronopathies (hereinafter abbreviated as "SNN") are a specific subgroup of peripheral nervous system diseases characterized by primary involvement of sensory neurons in the dorsal root ganglia (Kuntzer et al., Muscle Nerve, 2004; 30:255-268; Sghirlanzoni et al., Lancet Neurol., 2005; 4:349-361). SNNs encompass different paraneoplastic, viral, dysimmune, toxic, and idiopathic disorders.

Lesions in the dorsal root ganglia have been demonstrated pathologically in paraneoplastic SNN (Graus et al., Neurology, 1990; 40:219-222; Dalmau Jet al., Neurology 1991; 41:1757-1764; Wanschitz et al. Neurology, 1997; 49:1156-1159.), HIV infection (Scaravilli et al., Acta. Neuropathol. (Berl), 1992; 84:163-170; Esiri et al., J. Neurol. Sci., 1993; 114:178-187), Sjögren's syndrome (Mori et al., Brain, 2005; 128:2518-2534; Griffin et al., Ann. Neurol., 1990; 27:304-315), and unclassified connective diseases, but also in some idiopathic cases (Okajima et al., Neurology, 1983; 33:1061-1064; Sobue et al., Neurology, 1988; 38:463-467; Hainfellner et al., Ann. Neurol., 1996; 39:543-547; Kurokawa et al., J. Neurol. Neurosurg. Psychiatry, 1998; 65:278-279; Colli et al., Surg. Neurol., 2008; 69:266-273).

Recently, a set of clinical criteria that help to differentiate SNN from other sensory neuropathies has been published, but these criteria do not allow SNN to be distinguished according to their etiologies (Camdessanche et al., Brain, 2009; 132:1723-1733).

In particular, among SNN without an overt associated autoimmune context, it is at present not possible to distinguish on clinical grounds autoimmune SNN from non autoimmune idiopathic forms.

In addition, as these criteria were deliberately conceived to be stringent, they probably miss incomplete forms of SNN. As biopsy of dorsal root ganglia is not feasible as a routine investigation and because of the absence of methods that allow easy and non-traumatic exploration of dorsal root ganglia, there is a need for biological tools that may help to distinguish SNN from the far more numerous other form of sensory neuropathies.

Auto-antibodies reactive with sensory neuron antigens, mainly auto-antibodies called anti-Hu antibodies, have been identified in paraneoplastic SNN only (Camdessanche et al., Brain, 2009; 132:1723-1733; Graus et al., J. Neurol. Neurosurg. Psychiatry, 2004; 75:1135-1140; Camdessanche et al., Brain, 2002; 125:166-175; U.S. Pat. No. 6,193,948). A handful of studies using the serum of occasional patients with SNN and Sjögren's syndrome or idiopathic SNN tested on various substrates gave inconclusive results (Murata et al., Neuroreport., 2005; 16:677-681; Eystathioy et al., J. Mol. Med., 2003; 81:811-818; Dalakas M C, Ann. Neurol., 1986; 19:545-554; Nemni et al., Ann. Neurol., 1993; 34:848-854; van Dijk et al., J. Neuroimmunol., 1997; 74:165-172; Mutoh et al., Arch. Neurol., 2005; 62:1612-1615).

Differentiating SNN from other sensory neuropathies is important owing to the possibility of detecting disorders that may benefit from specific investigations and treatments.

Further, knowing whether an autoimmune process is involved in idiopathic cases or a subgroup of these is important, since it may lead to the development of immunomodulatory treatments and help to distinguish these cases from other sensory neuropathies.

The inventors have now shown that serum immunoreactivity toward fibroblast growth factor receptor (FGFR) family and related proteins, as well as toward proteins that belong to growth factor receptor-bound protein family, identify a subgroup of patients with SNN in which a dysimmune process is involved, suggesting that this subgroup of patients may be treated with immunosuppressants and/or immunomodulators.

DESCRIPTION OF THE INVENTION

In an attempt to find biomarkers which allow acquired sensory neuronopathies (SNN) to be distinguished from other neuropathies, the inventors unexpectedly found that a subgroup of patients who suffer from acquired sensory neuronopathy show an immunoreactivity toward a protein of the fibroblast growth factor receptor (FGFR) family, in particular toward FGFR3 (in particular toward the intracellular kinase domain of FGFR3, and/or TRK1 and/or TRK2 subunits of the intracellular kinase domain of FGFR3), FGFR1 and FGFR2, and to a lesser extent toward a protein that belongs to growth factor receptor-bound protein family, in particular growth factor receptor-bound protein 10 (GRB10). In this subgroup of patients suffering from SSN, most of the patients had no known associated autoimmune context.

Thus, the inventors have demonstrated for the first time that the presence in a sample from a patient of antibodies directed against proteins or fragments of proteins that belong to the fibroblast growth factor receptor (FGFR) family and/or against a protein or a fragment of a protein of the growth factor receptor-bound protein family can be used to discriminate between acquired sensory neuronopathies (SNN) and other neuropathies, in particular other sensory neuron disorders.

For instance, a patient diagnosed with a condition thought to be either proximal demyelinating polyneuropathy (abbreviated as "P-CIDP") or SNN and another patient with a condition thought to be either a distal sensory neuropathy were firmly diagnosed as suffering from SNN after detection of anti-FGFR3 antibodies.

The inventors also noted that sera from some patients immunopositive toward FGFR3 showed a cross immunoreactivity toward FGFR1 and/or FGFR2.

The inventors further noted that the patients afflicted with SNN who show immunoreactivity toward a member of the FGFR family, in particular toward FGFR3, and/or toward a protein of the GRB family, have specific clinical characteristics which distinguish their neuronopathies from both anti-Hu associated SNN and FGFR3 sero-negative SNN. In particular, they are younger, more frequently women, the neuropathy has a progressive course, although a subacute and sometimes acute evolution is possible. Another striking clinical feature is the frequent trigeminal nerve involvement at onset and asymmetrical distribution of sensory manifestations at full development. Some patients may present with small fiber neuropathy or trigeminal nerve neuropathy.

Interestingly, FGFR3 antibodies were also detected in some patients suffering from autoimmune diseases, but without previously identified neurological disorders. When going back to their file, it was found that these patients with FGFR3 antibodies did in fact suffer from sensory neuron disorders, thereby strengthening the value of FGFR3 antibodies as biomarkers for the diagnosis of a subgroup of SNN.

SUMMARY OF THE INVENTION

Therefore, the present invention relates to a method of determining if a patient is afflicted with an acquired sensory neuronopathy, said method comprising:

a) detecting in a biological sample of the patient immunoreactivity toward a protein of the tyrosine kinase receptor family and/or toward a protein of the growth factor receptor-bound protein family; and optionally b) deducing from the result of step a) whether the patient is afflicted with an acquired sensory neuronopathy, immunoreactivity toward a protein of the tyrosine kinase receptor family and/or toward a protein of the growth factor receptor-bound protein family is indicative of an acquired sensory neuronopathy.

The invention also relates to the use of antibody directed against a protein of the tyrosine kinase receptor family and/or of antibody directed against a protein of the growth factor receptor-bound protein family as a biomarker for diagnosing (or confirming) an acquired sensory neuronopathy in a patient.

The present invention also provides a method for selecting a patient afflicted with an acquired sensory neuronopathy suitable to be treated with at least one immunosuppressant and/or immunomodulator compound, comprising:

a) detecting in a biological sample of the patient immunoreactivity toward a protein of the tyrosine kinase receptor family and/or toward a protein of the growth factor receptor-bound protein family; and optionally b) selecting the patient as suitable to be treated with at least one immunosuppressant and/or immunomodulator compounds when immunoreactivity toward a protein of the tyrosine kinase receptor family and/or toward a protein of the growth factor receptor-bound protein family is detected.

The above methods of the invention may be, for instance, in vitro or ex vivo methods.

The invention also concerns a method for treating a patient suffering from an acquired sensory neuronopathy who shows immunoreactivity toward a protein of the tyrosine kinase receptor family and/or toward a protein of the growth factor receptor-bound protein family, which method comprises administering to the patient immunosuppressant and/or immunomodulator compounds, or a pharmaceutical composition comprising said compounds.

The invention also provides immunosuppressant and/or immunomodulator compounds, or a pharmaceutical composition thereof, for use in the treatment of a patient who suffers from an acquired sensory neuronopathy and who shows immunoreactivity toward a protein of the tyrosine kinase receptor family and/or toward a protein of the growth factor receptor-bound protein family.

The invention further provides a kit for diagnosing an acquired sensory neuronopathy and a kit for selecting a patient afflicted with an acquired sensory neuronopathy suitable to be treated with at least one immunosuppressant and/or immunomodulator compounds, as described below.

It is to be understood that the methods, use and kits of the invention are not intended to identify or select patients suffering from any types of acquired sensory neuronopathy (SNN), but only to identify/select a specific subset of patients afflicted with an acquired sensory neuronopathy. It is not excluded that patients who are not identified by the methods, use and kits of the invention belong to another subset of patients afflicted with SNN.

DETAILED DESCRIPTION OF THE INVENTION

These and other objects, features and advantages of the invention will be disclosed in the following detailed description.

The present invention relates to a method of determining if a patient is afflicted with an acquired sensory neuronopathy, said method comprising:

a) detecting in a biological sample of the patient immunoreactivity toward a protein of the tyrosine kinase receptor family and/or toward a protein of the growth factor receptor-bound protein family; and optionally b) deducing from the result of step a) whether the patient is afflicted with an acquired sensory neuronopathy, immunoreactivity toward a protein of the tyrosine kinase receptor family and/or toward a protein of the growth factor receptor-bound protein family is indicative of an acquired sensory neuronopathy.

The present invention also relates to the use of antibody directed against a protein of the tyrosine kinase receptor family and/or of antibody directed against a protein of the growth factor receptor-bound protein family as a biomarker for diagnosing (or confirming) an acquired sensory neuronopathy in a patient.

In a preferred embodiment, the patient to be tested is suffering, or is suspected to be suffering, from a neuropathy, preferably a sensory neuropathy.

A neuropathy is defined as a disorder of the peripheral nervous system, involving at least one of its motor, sensory or autonomic components. Each component includes the neuron cell body, its axons and the myelinating or non myelinating Schwann cells wrapping the axon. These components can be injured in the spinal cord anterior horns (motor neurons), in the dorasal root ganglia (sensory neurons) in the autonomic ganglia (autonomic neurons) and in the peripheral nerve including roots, plexus and nerves proper in which the axons circulate (see Dyck, Thomas, Lambert, Bunge. Peripheral Neuropathy. Vol. II. W.B. Saunders Co, Philadelphia, Pa. 1984).

A sensory neuropathy is defined as an exclusive or predominant involvement of sensory neurons with their axons and/or surrounding Schwann cells (see Dyck, Thomas, Lambert, Bunge. Peripheral Neuropathy. Vol. II. W.B. Saunders Co, Philadelphia, Pa. 1984). This disease includes sensory neuronopathies, distal or length dependent sensory neuropathies, small fiber neuropathies and sensory forms of chronic inflammatory demyelinating polyneuropathies, and focal sensory neuropathies such as trigeminal nerve neuropathies.

In another preferred embodiment, the patient to be tested is suspected to be suffering from an acquired sensory neuronopathies (SNN) and the method is performed to confirm that the patient is actually afflicted with this disease.

In a third embodiment, the patient to be tested is afflicted with lupus and/or Sjögren syndrome and is suffering from sensory symptoms or neuropathic pain and the method is performed to determine if the patient is actually afflicted with SNN.

The present invention also provides an in vitro method for selecting a patient afflicted with an acquired sensory neuronopathy suitable to be treated with at least one immunosuppressant and/or immunomodulator compound, comprising:

a) detecting in a biological sample of the patient immunoreactivity toward a protein of the tyrosine kinase receptor family and/or toward a protein of the growth factor receptor-bound protein family; and optionally b) selecting the patient as suitable to be treated with at least one immunosuppressant and/or immunomodulator compounds when immunoreactivity toward a protein of the tyrosine kinase receptor family and/or toward a protein of the growth factor receptor-bound protein family is detected.

The method of determining if a patient is afflicted with an acquired sensory neuronopathy, the use of antibody directed against a protein of the tyrosine kinase receptor family and/or of antibody directed against a protein of the growth factor receptor-bound protein family as a biomarker for diagnosing (or confirming) an acquired sensory neuronopathy, and the method of selecting a patient afflicted with an acquired sensory neuronopathy suitable to be treated with at least one immunosuppressant and/or immunomodulator compound of the invention may be, for instance, in vitro or ex vivo methods.

The invention also concerns a method for treating a patient suffering from an acquired sensory neuronopathy who shows immunoreactivity toward a protein of the tyrosine kinase receptor family and/or toward a protein of the growth factor receptor-bound protein family, which method comprises administering to the patient immunosuppressant and/or immunomodulator compounds, or a pharmaceutical composition comprising said compounds.

The invention also provides immunosuppressant and/or immunomodulator compounds, or a pharmaceutical composition comprising said compounds, for use in the treatment of a patient suffering from an acquired sensory neuronopathy who shows immunoreactivity toward a protein of the tyrosine kinase receptor family and/or toward a protein of the growth factor receptor-bound protein family.

In some embodiments, the protein of the tyrosine kinase receptors family against which immunoreactivity is tested is a protein of the fibroblast growth factor receptor (abbreviated as "FGFR") family or a protein of the tropomyosin-receptor-kinase (abbreviated as "Trk") family.

In particular embodiments, the protein against which immunoreactivity is tested is a protein of the FGFR family chosen from the group consisting of receptors FGFR1 (e.g. NCBI accession number NP_075598.2 (SEQ ID NO: 1); NCBI accession number NP_075594.1 (SEQ ID NO: 2)), FGFR2 (e.g. NCBI accession number NP_000132.3 (SEQ ID NO: 3); NCBI accession number AAH39243 (SEQ ID NO: 4)), FGFR3 (e.g. NCBI accession number NP_000133; SEQ ID NO: 5) and FGFR4 (e.g. NCBI accession number NP_998812.1; SEQ ID NO: 6). In another particular embodiment, the protein against which immunoreactivity is tested is FGFR3.

The member of the FGFR family are structurally related proteins which exhibit an extracellular domain composed of three immunoglobin-like domains which form the ligand-binding domain, an acid box, a single transmembrane domain and an intracellular split tyrosine kinase domain. Multiple forms of FGFR-1 to -3 are generated by alternative splicing of the mRNAs. The extracellular portion of the protein interacts with fibroblast growth factors, setting in motion a cascade of downstream signals, ultimately influencing mitogenesis and differentiation. This kinase domain interacts with different proteins responsible of the downstream effects of FGF fixation on their receptors. This includes proteins of the GRB family.

In another embodiment, the protein against which immunoreactivity is tested is a protein of the Trk family, preferably chosen from the group consisting of receptors TrkA (e.g. NCBI accession number NP_001007793.1, also known as "neurotrophic tyrosine kinase receptor type 1"; SEQ ID NO: 7), TrkB (e.g. NCBI accession number NP_001007098.1, also known as "neurotrophic tyrosine kinase receptor type 2"; SEQ ID NO: 8) and TrkC (e.g. NCBI accession number NP_001007157.1, also known as "neurotrophic tyrosine kinase receptor type 3"; SEQ ID NO: 9). Trk receptors are a family of tyrosine kinases that regulates synaptic strength and plasticity in the mammalian nervous system.

In another embodiment, the protein against which immunoreactivity is tested is a protein of the growth factor receptor-bound protein (abbreviated as "GRB") family, preferably chosen from the group consisting of GRB1 to GRB14. More preferably, the protein of the growth factor receptor-bound protein family is GRB10 (for instance the GRB10 coded for by the polynucleotide sequence with NCBI accession number NM_001001550.1; SEQ ID NO: 10). GRB proteins are adaptor proteins involved in signal transduction triggered by activated tyrosine kinase receptors.

In a particularly advantageous embodiment, the protein(s) against which immunoreactivity is tested are at least FGFR3 and/or GRB10.

As used herein, reference to the "tyrosine kinase receptors", the "FGFR receptors", "Trk receptors", and "GRB proteins" refer to all of the naturally-occurring variants, such as splice variants, allelic variants and isoforms, of said receptors or proteins.

In particular, the terms tyrosine kinase receptors, the FGFR, Trk receptor, or "GRB proteins" refer to:
a) the polypeptide comprising or consisting of the amino acid sequence shown in NCBI accession number as recited above (for instances SEQ ID Nos: 1 to 10); and/or
b) a polypeptide corresponding to the mature isoform of a polypeptide of (a) (i.e. obtained after cleavage of the signal peptide); and/or
c) an allelic variant of a polypeptide of (a) or (b); and/or
d) a splice variant of a polypeptide of (a), (b) or (c); and/or
e) a constitutively active mutant of a polypeptide of (a), (b), (c) or (d).
f) an isoform obtained by proteolytic processing of a polypeptide of (a), (b), (c), (d) or (e).

By "variant of a polypeptide" is meant a polypeptide that has at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% amino acid sequence identity to a full-length polypeptide reference sequence. In the context of the present application, the percentage of identity is calculated using a global alignment (i.e. the two sequences are compared over their entire length). Methods for comparing the identity of two or more sequences are well known in the art. The <<needle>> program, which uses the Needleman-Wunsch global alignment algorithm (Needleman and Wunsch, 1970 J. Mol. Biol. 48:443-453) to find the optimum alignment (including gaps) of two sequences when considering their entire length, may for example be used. The needle program is for example available on the ebi.ac.uk world wide web site. The percentage of identity in accordance with the invention is preferably calculated using the EMBOSS::needle (global) program with a "Gap Open" parameter equal to 10.0, a "Gap Extend" parameter equal to 0.5, and a Blosum62 matrix.

As used herein, a "constitutively active mutant of a receptor (polypeptide) refers to a mutant of said receptor exhibiting a biological activity (i.e. triggering downstream signaling) in the absence of stimulation by its ligand, and/or exhibiting a biological activity which is higher than the biological activity of the corresponding wild-type receptor in the presence of its ligand.

As used throughout the present application, the expression "Immunoreactivity toward a target protein" (here a member of the receptor-tyrosine kinase family or a member of the growth factor receptor-bound protein family) is intended to mean that the sample from the patient to be tested comprises antibodies specifically directed against the target protein or a fragment of this target protein.

Therefore, immunoreactivity toward a target protein can be easily detected by demonstrating in the biological sample to be tested the presence of antibodies specifically directed against the target protein or a fragment of this target protein.

Fragments of the target proteins may be truncated at the N-terminus or C-terminus, or may lack internal residues, for example, when compared with a full length protein. Preferably, said fragments are at least about 10, 20, 30, 40, 50, 60, 70, 80, 90, 100, 110, 120, 150, 250, 300, 350, 400, 450, 500 or more amino acids in length.

Such a test can be performed by one of ordinary skill in the art by using standard methods, for instance Enzyme-linked immunosorbent assay ("ELISA"), Western Blot/Dot Blot, Immunohistochemistry on transfected cells, Luminex (see for review Immunodiagnostics: A Practical Approach, R. Edwards Editor, Oxford University Press 2000; Manual of Molecular And Clinical Laboratory Immunology, J. D. Folds R. G. Hamilton, B. Detrick Editors ASM Press 2006; Immunology and Serology in Laboratory Medicine, M. L. Turgeon, Mosby Inc, 2008).

For instance, for determining the presence of anti-FGFR3 antibodies in a sample, the target protein can consist of, or comprise, the full-length FGFR3 receptor, the intracellular part of FGFR3, the intracellular kinase domain of FGFR3, the TRK1 and/or TRK2 subunits of the intracellular kinase domain of FGFR3, or a fragment thereof. Preferably the target protein consists of, or comprises, the intracellular kinase domain of FGFR3 (i.e. a fragment of a FGFR3 protein corresponding to fragment spanning the amino acid at position 397 or 399 to the amino acid at position 806, positions being given according to FGFR3 of NCBI accession number NP_000133), the TRK1 subunit of the intracellular kinase domain of FGFR3 (i.e. a fragment of a FGFR3 protein corresponding to fragment spanning the amino acid at position 403 to the amino acid at position 660, positions being given according to FGFR3 of NCBI accession number NP_000133), the TRK2 subunit of the intracellular kinase domain of FGFR3 (i.e. a fragment of a FGFR3 protein corresponding to fragment spanning the amino acid at position 661 to the amino acid at position 792, positions being given according to FGFR3 of NCBI accession number NP_000133) or a fragment thereof.

More preferably, the target protein consists of, or comprises, FGFR3 of NCBI accession number NP_000133 (SEQ ID NO: 5), TRK1 subunit of the intracellular kinase domain of FGFR3 of NCBI accession number NP_000133 (i.e. fragment 403-660 of FGFR3 of NCBI accession number NP_000133; SEQ ID NO: 12), or TRK2 subunit of the intracellular kinase domain of FGFR3 of NCBI accession number NP_000133 (i.e. fragment 661-792 of FGFR3 of NCBI accession number NP_000133; SEQ ID NO: 13).

Advantageously, the target protein consists of, or comprises, the intracellular kinase domain consisting of the amino acid sequence that spans amino acids 397 to 806 (SEQ ID NO: 11) or 399 to 806 of FGFR3 of NCBI accession number NP_000133 or a fragment thereof.

The terms "antibody" and "immunoglobulin" have the same meaning, and are used indifferently in the present invention.

The term "antibody" refers to immunoglobulin molecules and immunologically active portions of immunoglobulin molecules, i.e., molecules that contain an antigen binding site that immunospecifically binds to specific epitope on the target protein.

In the context of the invention, the "biological sample" is preferably blood, serum, plasma or cerebrospinal fluid from the patient to be tested. More preferably, the biological sample is serum.

The term "immunosuppressant" (also called "immunodepressant") refers to compounds that can suppress or prevent the immune response. Immunosuppressants are commonly used to prevent rejection of a transplanted organ and to treat autoimmune diseases, and are well known to a person of ordinary skill in the art. For instance, mention may be made of tacrolimus (CAS number 104987-11-3), cyclosporine (CAS number 59865-13-3), methotrexate (CAS number 59-05-2), glucocorticoids such as cortisol (CAS number 50-23-7), prednisone (CAS number 53-03-2), prednisolone (CAS number 50-24-8), methylprednisolone (CAS number 83-43-2), dexamethasone (CAS number 50-02-2), betamethasone (CAS number 378-44-9), cyclophosphamide (CAS number 50-18-0), azathioprine (CAS number 446-86-6), mycophenolate mofetil (CAS number 24280-93-1), plasma exchanges, intravenous immunoglobulins, compounds that target B cells (e.g. anti-CD20 antibodies) or T-cells activation, compounds (for instance fingolimod, CAS number 162359-55-9) that block efference from lymphoid organs (i.e. migration of mature leukocytes/lymphocytes from lymphoid organs) (see for instance Umapathi T, Hughes R A, Nobile-Orazio E, Léger J M, Immunosuppressant and immunomodulatory treatments for multifocal motor neuropathy, Cochrane Database Syst Rev. 2012 Apr. 18; 4:CD003217; Dalakas M C; Medscape, Advances in the diagnosis, pathogenesis and treatment of CIDP, Nat Rev Neurol. 2011 Aug. 16; 7(9):507-17; Kieseier B C, Lehmann H C, Meyer Z u Hörste G, Autoimmune diseases of the peripheral nervous system, Autoimmun Rev. 2012 January; 11(3):191-5; Walgaard C, Jacobs B C, van Doorn P A, Emerging drugs for Guillain-Barré syndrome, Expert Opin Emerg Drugs. 2011 March; 16(1):105-20; Hutton E J, Lunn M P, Treatment in inflammatory neuropathies. Expert Rev Clin Immunol. 2010 March; 6(2):231-45; Tracy J A, Dyck P J, Investigations and treatment of chronic inflammatory demyelinating polyradiculoneuropathy and other inflammatory demyelinating polyneuropathies, Curr Opin Neurol. 2010 June; 23(3):242-8).

As used herein, the term "patient" denotes a human being.

In the context of the invention, the term "treating" is used herein to characterize a therapeutic method or process that is aimed at (1) slowing down or stopping the progression, aggravation, or deterioration of the symptoms of the disease state or condition to which such term applies; (2) alleviating or bringing about ameliorations of the symptoms of the disease state or condition to which such term applies; and/or (3) reversing or curing the disease state or condition to which such term applies.

The immunosuppressants and immunomodulators used in the above recited method or use for treating patients afflicted with SNN are provided in a pharmaceutically acceptable carrier, exipient or diluent which is not prejudicial to the patient to be treated.

Pharmaceutically acceptable carriers and exipient that may be used in the compositions of this invention include, but are not limited to, ion exchangers, alumina, aluminium stearate, lecithin, self-emulsifying drug delivery systems (SEDDS) such as d-a-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

As appreciated by skilled artisans, compositions are suitably formulated to be compatible with the intended route of administration. Examples of suitable routes of administration include parenteral route, including for instance intramuscular, subcutaneous, intravenous, intraperitoneal or local intratumoral injections. The oral route can also be used, provided that the composition is in a form suitable for oral administration, able to protect the active principle from the gastric and intestinal enzymes.

Further, the amount of immunosuppressants and/or immunomodulators used in the above recited method or use for treating patients afflicted with SNN is a therapeutically effective amount. A therapeutically effective amount of immunosuppressants and/or immunomodulators is that amount sufficient to suppress (by at least about 10%, preferably by at least about 30%, preferably by at least about 50%, preferably by at least about 70, 75 or 80%, still preferably by 85, 90, 95, or 100%) the immune response, preferably the immune response specifically directed toward tyrosine kinase receptors, the FGFR, Trk receptor, and/or "GRB proteins" against which the patient shows immunoreactivity, or to treat a desired disease without causing overly negative effects in the subject to which the immunosuppressants and/or immunomodulators are administered.

The exact amount of immunosuppressants and/or immunomodulators to be used and the composition to be administered will vary according to the age and the weight of the patient being treated, the type of disease, the mode of administration, the frequency of administration as well as the other ingredients in the composition which comprises the immunosuppressants and/or immunomodulators. Such concentrations can be routinely determined by those of skilled in the art. The amount of the immmunoglobulin actually administered will typically be determined by a physician, in the light of the relevant circumstances, including the condition to be treated, the chosen route of administration, the actual immunosuppressants and/or immunomodulators administered, the age, weight, and response of the individual patient, the severity of the patient's symptoms, etc.

Generally, the immunosuppressants and/or immunomodulators used in the above recited method or use for treating patients afflicted with SNN may be administered in the typical range. Effective doses will also vary depending on route of administration, as well as the possibility of co-usage with other agents. For instance, typical dose of prednisone can be 1 mg/kg/day, that of tacrolimus 0.10-0.20 mg/kg/day, that of cyclosporine 2-6 mg/kg/day, that of methotrexate 7.5-15 mg/week, that of cyclophosphamide 500 mg/m2 every month, that of azathioprine 150 mg/day, that of micophenolate mophetil 2 g/day, that of intravenous immunoglobulins 0.4 g/kg/day for 4 days, that of or rituximab 375 mg/m2 every week for four weeks or 2 infusions of 1000 mg at 2 weeks interval.

The invention further provides kits that are useful in the above methods for diagnosing an acquired sensory neuronopathy or for selecting a patient afflicted with an acquired sensory neuronopathy suitable to be treated with at least one immunosuppressant and/or immunomodulator compounds.

Such kits comprise means for detecting antibodies directed toward at least one protein of the tyrosine kinase receptor family and/or toward at least one protein of the growth factor receptor-bound protein family.

Preferably, the kit comprises at least means for detecting antibodies directed toward FGFR3, the intracellular part of FGFR3 and/or the intracellular kinase domain of FGFR3, and/or GRB10 (preferably a GRB10 protein coded for by the polynucleotide sequence SEQ ID NO: 10). Still preferably, in one embodiment the kit consists of means for detecting antibodies directed toward FGFR3, the intracellular part of FGFR3 and/or the intracellular kinase domain of FGFR3 and/or the TRK1 and/or TRK2 subunits of the intracellular kinase domain of FGFR3, and means for detecting antibodies directed toward GRB10. Advantageously, the intracellular kinase domain of FGFR3 consists of the amino acid sequence that spans amino acids 397 to 806 (SEQ ID NO: 11) or 399 to 806 of FGFR3 of NCBI accession number NP_000133), the TRK1 subunit of the intracellular kinase domain of FGFR3 of NCBI accession number NP_000133 (i.e. fragment 403-660 of FGFR3 of NCBI accession number NP_000133; SEQ ID NO: 12), the TRK2 subunit of the intracellular kinase domain of FGFR3 of NCBI accession number NP_000133 (i.e. fragment 661-792 of FGFR3 of NCBI accession number NP_000133; SEQ ID NO: 13).

Such means can be the target protein(s), i.e. the protein(s) of the tyrosine kinase receptor family and/or of the growth factor receptor-bound protein family against which immunoreactivity is tested, or fragments thereof as described above.

For instance, when immunoreactivity toward FGFR3 is tested, the target(s) protein(s) is (are) preferably chosen from the group consisting of i) the full-length FGFR3 receptor, ii) a protein which consists of, or comprises, the intracellular kinase domain of FGFR3, iii) a protein which consists of, or comprises, the TRK1 subunit of the intracellular kinase domain of FGFR3, and iv) a protein which consists of, or comprises, the TRK2 subunit of the intracellular kinase domain of FGFR3, more preferably the target(s) protein(s) is (are) chosen from the group consisting of i) FGFR3 of NCBI accession number NP_000133 (SEQ ID NO: 5), ii) a protein which consists of, or comprises, the intracellular kinase domain consisting of the amino acid sequence that spans amino acids 397 to 806 (SEQ ID NO: 11) or 399 to 806 of FGFR3 of NCBI accession number NP_000133, iii) a protein which consists of, or comprises, the TRK1 subunit of the intracellular kinase domain of FGFR3 of NCBI accession number NP_000133 (i.e. fragment 403-660 of FGFR3 of NCBI accession number NP_000133; SEQ ID NO: 12), and iv) a protein which consists of, or comprises, the TRK2 subunit of the intracellular kinase domain of FGFR3 of NCBI accession number NP_000133 (i.e. fragment 661-792 of FGFR3 of NCBI accession number NP_000133; SEQ ID NO: 13). In a preferred embodiment, when immunoreactivity toward FGFR3 is tested, the target(s) protein(s) comprise(s) at least a protein which consists of, or comprises, the intracellular kinase domain consisting of the amino acid sequence that spans amino acids 397 to 806 (SEQ ID NO: 11) or 399 to 806 of FGFR3 of NCBI accession number NP_000133.

For instance, when immunoreactivity toward GRB10 is tested, the target protein consists of all or part of GRB10, preferably all or part of a GRB10 protein coded for by the polynucleotide sequence SEQ ID NO: 10.

For instance, when immunoreactivity toward FGFR1 is tested, the target protein consists of all or part of FGFR1, preferably all or part of a FGFR1 protein of SEQ ID NO: 1 or of SEQ ID NO: 2.

When immunoreactivity toward FGFR2 is tested, the target protein, for instance, consists of all or part of FGFR2, preferably all or part of a FGFR2 protein of SEQ ID NO: 3 or of SEQ ID NO: 4.

Means for detecting antibodies directed toward at least one protein of the tyrosine kinase receptor family and/or toward at least one protein of the growth factor receptor-bound protein family may also include an antibody specifically binding to human antibodies (used as a "secondary antibody" which binds to antibodies from the sample to be tested specifically binding to the target protein). Such antibodies can be labeled with detectable compound such as fluorophores or radioactive compounds.

In a preferred embodiment, the kit according to the invention may further comprises a control sample comprising a known amount of antibodies and/or instructions for the use of said kit in diagnosing an acquired sensory neuronopathy or in selecting a patient afflicted with an acquired sensory neuronopathy suitable to be treated with at least one immunosuppressant and/or immunomodulator compounds.

The means may be present, e.g., in vials or microtiter plates, or be attached to a solid support. For instance the target protein can be attached to a membrane or to an array.

All references cited herein, including journal articles or abstracts, published patent applications, issued patents or any other references, are entirely incorporated by reference herein, including all data, tables, figures and text presented in the cited references.

The invention will be further evaluated in view of the following examples and figures.

Comparison of the mean OD (optical density) minus blank value in the groups (ANOVA test) is presented: D=blood donors; lupus/SGS=autoimmune diseases; other neurop=other neuropathies; SNN=sensory neuronopathies. The patient and control groups are on the x-axis and the OD values minus blank values are on the y-axis.

Figure 4:
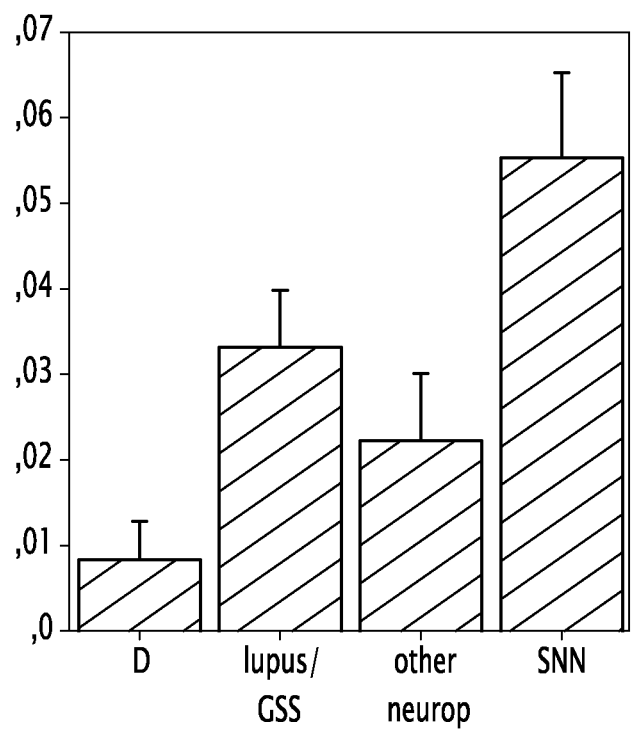

FIG. 4 is a histogram which illustrates the results of ELISA assays carried out on sera from patients suffering from autoimmune diseases or neuropathies, with the human FGFR3 399-806 aa peptide corresponding to the protein intracellular domain.

Comparison of the normalized OD in four groups (ANOVA test) is presented: D=blood donors; lupus/SGS=autoimmune diseases; other neurop=other neuropathies; SNN=sensory neuronopathies. The patient and control groups are on the x-axis and the normalised OD values are on the y-axis.

Figure 5:
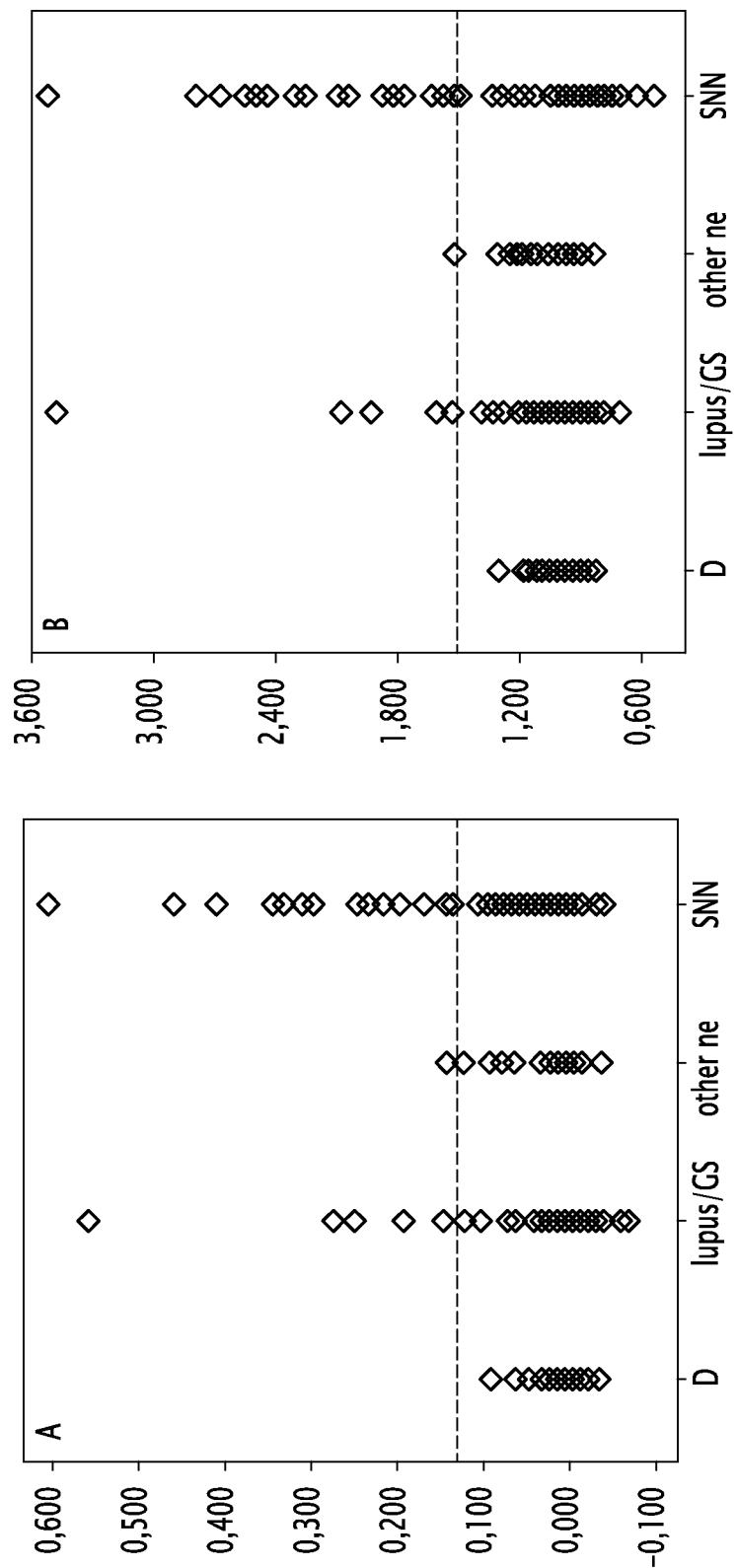

FIG. 5 illustrates the results of ELISA assays with the human FGFR3 399-806 aa peptide corresponding to the protein intracellular domain.
Part A: normalised OD.
Part B: index.
D=blood donors; lupus/SGS=autoimmune diseases; other neurop=other neuropathies; SNN=sensory neuronopathies.
The dotted line indicates the cut-off level.

EXAMPLES

Example 1

Materials and Methods 1.1. Serum Samples

Serum samples from 261 individuals were collected. Sera were snap frozen at −80° C. and stored until utilisation. Individuals were classified into four groups. Group I corresponded to 59 healthy blood donors. Group II included 56 patients with systemic autoimmune diseases and lupus or Sjögren syndrome antibodies, group III included 104 patients with a diagnosis of sensory neuropathy, and group IV included 42 patients with sensorimotor peripheral neuropathies. Among group III, the neuropathy was a probable or possible SNN according to published criteria in 85 patients (Camdessanche J. P. et al., Brain 2009; 132:1723-1733). Among the 19 who did not fill these criteria, 7 had small fiber SNN and 2 a sensory neuropathy that could not be distinguished between proximal demylinating polyneuropathy (P-CIDP) and SNN. In the other, the criteria were not fulfilled mainly because ENMG sensory nerve abnormalities were mild. A known dysimmune context was associated with the neuropathy in 72/104 patients including, Sjögren syndrome, lupus, lupus anticoagulant, unclassified connective disorders, monoclonal gammopathy, including CANOMAD syndrome, and HIV infection. Eight had paraneoplastic SNN with Hu antibodies. Patients in group IV had Guillain-Barré syndrome, chronic inflammatory demyelinating polyneuropathy, multifocal motor neuropathy, neuropathy with monoclonal gammopathy, mononeuritis multiplex with vasculitis, diabetic neuropathy, hereditary neuropathy or idiopathic length dependent axonal neuropathy. As a whole the neuropathy was dysimmune in 11/42.

1.2. Protein Arrays

Sera were probed in the human ProtoArray v.4.2 (Invitrogen, Carlsbad, N. Mex., USA). These microarrays contained 9000 human GST-tagged proteins, expressed in Sf9 insect cells and spotted in duplicate. Protoarrays were used according to the recommendations of the manufacturer. Briefly, the slides were equilibrated at 4° C. for 15 min and then incubated with blocking buffer (50 mM Hepes, pH7.5, 200 mM Nacl, 0.08% Triton X-100, 25% Glycerol, 20 Mm Reduced glutathione, 1 mM DTT, 1X Roti-Block) for 1 h at 4° C. with gentle shaking. Then slides were incubated with human sera diluted 1:500 in washing buffer (1X PBS, 0.1% Tween 20, 1X Roti-Block) for 90 min at 4° C. with gentle shaking. Slides were washed five times with the washing buffer and incubated with 1 μg/ml of secondary antibodies (Alexa Fluor 647 goat anti-human IgG antibody; Invitrogen) to detect the Human bound antibodies. The arrays were washed and dried by centrifugation at 200 g for 1 min. An array used as a control was incubated with the secondary antibody for background determination. A protein gradient of purified human IgG printed on each subarray was used as a positive control. Finally, the slides were scanned using a Genepix 4000B scanner (Axon, Union City, Calif., USA) with the laser set at 635 mm, the laser power at 100%, and the photomultiplier gain at 800. GenePix Pro 3.0 image analysis software (Axon, Union City, Calif., USA) was used for the quantification. The ProtoArray Prospector v5.0 software was used to identify immunoreactivities. This software uses the Chebyshev inequality P value, which is derived by testing the null hypothesis. Two statistical tools were used to detect positive spots, CI p-value and z-score. They correspond respectively to the probability that a spot is similar to a negative control, and to the spot signal minus average (for all spots) divided by the standard deviation for all spots. The NNS serum samples were compared versus control serum samples to obtain significant protein hits. The software also calculates the z score for each printed spot's fluorescent intensity. The z score indicates the deviation of each protein's antibody reading from its distribution mean (SD).

1.3. Dot Blot

A dot blot was used to assess the ability of target proteins to screen for SNN status in serum. Two to 10 μl of the purified recombinant peptide consisting of the 399-806 aa of the protein corresponding to the intracellular kinase domain of human FGFR3 (Invitrogen) used for the ProtoArray was spotted in nitrocellulose membrane. The membrane dried for 5 min and was blocked with 5% BSA in TBS-T for 1 h. Then serum samples (dilution 1/50 in blocking buffer) were incubated overnight at 4° C. After washing three times, biotinylated goat anti anti-human IgG antibody (Dako, Glostrup, Denmark) diluted 1:100 in blocking buffer, followed by streptavidin-peroxidise was used. Immunoreactive spots were visualized using diaminobenzidine (DAB) detection reagents. As control, a rabbit polyclonal anti-FGFR3 antibody directed against the 742-806 aminoacide sequence of human FGFR3 (GeneTex, San Antonio, Tex., USA) was used.

1.4. ELISA

The ELISA method was used to assess the ability of target protein identified by protoarray analysis to screen for sensitive ganglionopathy status in serum. Briefly, microtiter plates (Maxisorp, Nunc) were coated overnight at 4° C. with 1 μg/ml of the purified recombinant intracellular domain of human FGFR3 (Invitrogen), the full length recombinant FGFR1 (NCBI Reference Sequence: NP_075594.1; SEQ ID NO: 2) or FGFR2 proteins (AAH39243; SEQ ID NO: 4 (Novus biologicals) in carbonate-bicarbonate 0.05 M pH 9.6 solution. After washing one time with washing buffer (PBS containing 0.1% Tween 20), plates were blocked with blocking buffer, washing buffer containing 3% SVF and 0.1% gelatine for 1 h at room temperature. Then, serum samples (dilution 1/50 in blocking buffer) were incubated for 1 h at room temperature. After washing four times with washing buffer, anti-human IgG peroxidase-labelled (dilution 1/3000 in blocking buffer) was added for 1 h à room temperature. Then the signal was developed with o-Phenylenediamine substrate for 15 min to 30 min (sigma) and read at 450 nm. Each serum was tested in duplicate and the mean optic density (OD) of the readings was taken into account for the analysis. Controls included blank wells containing the products of the reaction minus human sera and the secondary antibody. The rabbit polyclonal anti-FGFR3 antibody diluted at 1/1000 and the appropriate secondary antibody were used as control and to normalise readings among plates. The specific reactivity of patients or controls' samples was obtained by subtracting the readings of plates of a pool of sera from a panel of healthy blood donors from the readings of plates of tested sera (hereafter designated as the normalized OD). In addition to limit variation among tests an index was built as follows: (OD of the tested serum/OD of the blank wells)/(OD of the pool of control sera/OD of the blank wells). To be considered as positive, the serum must be positive both for the normalized OD and the index.

1.5. Expression of FGFR by Sensory Neurons.

Purified cultures of dorsal root ganglia (DRG) neurons were established from embryonic day 18 (E18) rats as previously described (Seilheimer B. et al., J. Cell. Biol. 1988; 107:341-351). Briefly, DRG were collected in L-15 medium (Gibco Invitrogen) containing antibiotics, centrifuged, and incubated for 15 min in 0.25% EDTA-trypsin (Gibco Invitrogen), then centrifuged and resuspended in MCM. The pellets were mechanically dissociated by passage through a 21 gauge needle and the neurons plated on poly-L-lysine-coated coverslips in MCM containing 50 ng/mL of recombinant human b-nerve growth factor (NGF, Peprothech, Rocky Hill, N.J., USA) and 5 mg/mL of glucose. After two days of cultures cells were fixed for 3 minutes in 5% paraformaldehyde and tested by immunohistochemistry with either anti-FGFR3, FGFR1, FGFR2 (GenTex), CRMP5 (home made) antibodies diluted at 1/500 and revealed either with FITC-conjugated goat anti-rabbit IgG antibody (Sigma-Aldrich) at a 1:1000 dilution or rhodamine-conjugated goat anti-mouse IgG antibody (Sigma-Aldrich) at a 1:2000 dilution. Double-immunolabelling was performed by incubating the sample with the primary antibodies under the conditions described above, followed by the appropriate FITC- and rhodamine-conjugated antibodies.

1.6. Immunocytochemistry on HEK293 Cells.

HEK293 cells were transfected with plasmids containing the full length (pEGFPN3-FGFR3 full lengh), the intracellular domain (i.e. fragment which spans amino acids 397 to 806 of FGFR3) (pEGFPN3-FGFR3 cytoplasmic domain), the TRK1 (pEGFPN3-FGFR3-TK1 domain) or the TRK2 (pEGFPN3-FGFR3-TK2 domain) subunits of the intracellular domain of human FGFR3 tagged with EGFP or plasmid without insert (control).

The plasmids pEGFPN3-FGFR3 full lengh, pEGFPN3-FGFR3 cytoplasmic domain, pEGFPN3-FGFR3-TK1 domain and pEGFPN3-FGFR3-TK2 domain were amplified from pcDNA3-hFGFR3 (a generous gift from Dr. Vigdis Sorensen, University of Oslo, Norway) by the following primers:

5'ATGGGCGCCCCTGCCTGC3' (SEQ ID NO: 14) and 5'CGTCCGCGAGCCCCCAC3' (SEQ ID NO: 15) for pEGFPN3-FGFR3 full lengh.

5'ATGAAGAAAGGCCTGGGCTCC3' (SEQ ID NO: 16) and 5'CGTCCGCGAGCCCCCAC3' (SEQ ID NO: 17) for pEGFPN3-FGFR3 cytoplasmic domain 5'ATGAAGAAAGGCCTGGGCTCC3' (SEQ ID NO: 18) and 5'CCACTTCACGGGCAGCC 3' (SEQ ID NO: 19) for pEGFPN3-FGFR3-TK1 domain 5'ATGGCGCCTGAGGCCTTG3' (SEQ ID NO: 20) and 5'CGTCCGCGAGCCCCCAC3' (SEQ ID NO: 21) for pEGFPN3-FGFR3-TK2 domain The PCR product was cut with Hind III and BamH1 and ligated into EGFP-N3 vector (Clontech laboratories).

HEK293 cells were cultured in Dulbecco's modified minimal essential medium (DMEM, Gibco) containing 10% fetal bovine serum (FBS, Gibco) and antibiotics (25 U/ml penicillin and 25 µg/ml streptomycin and amphotericin) at 37° C. with 5% CO2. The day before transfection, the HEK293 cells were seeded into 24 well culture plates (9.104 per well).

HEK293 cells were transfected using lipofectamine LTX (Invitrogen). A 100 µl mix containing 0.5 µg plasmidic DNA and 1.5 µl lipofectamine in OPTI-MEM medium (Invitrogen) was added to each well for 48 h at 37° C.

Cells were then fixed in 4% paraformaldehyde for 5 min, washed with PBS. The cells were then blocked and permeabilized with 0.2% gelatin buffer containing 0.1% triton X-100 at room temperature for 1 h before being incubated overnight at 4° C. with patient's sera (diluted 1/20). After incubation, cells were rinsed with PBS and incubated with TRITC-goat anti-human IgG (Interchim) diluted 1/2000 for 3 h at 4° C.

Immunostaining was observed with Zeiss fluorescence microscope.

Example 2

Figure 1:
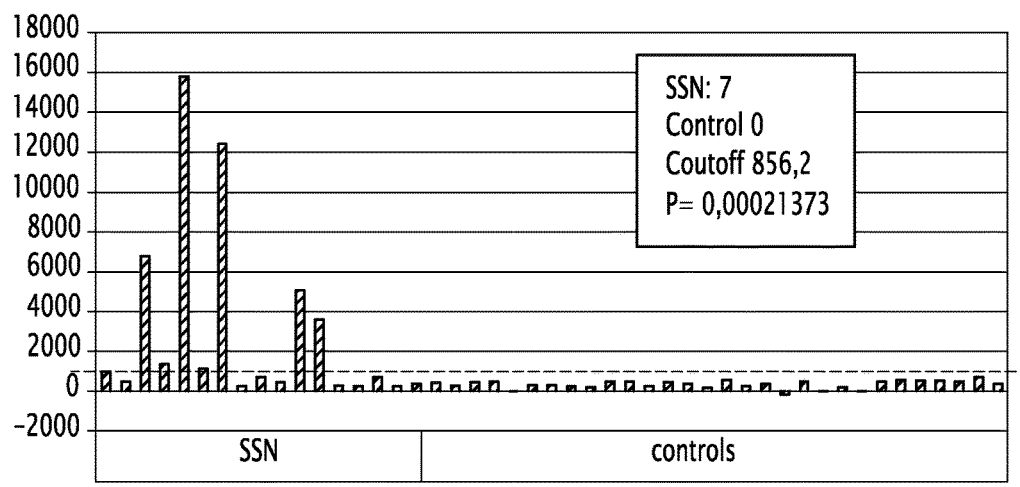
FIG. 1 illustrates the level of reactivity of 16 non paraneoplastic SNN and 30 controls on FGFR3. The dotted line indicates the cut-off level. Protoarray assay
Figure 2:
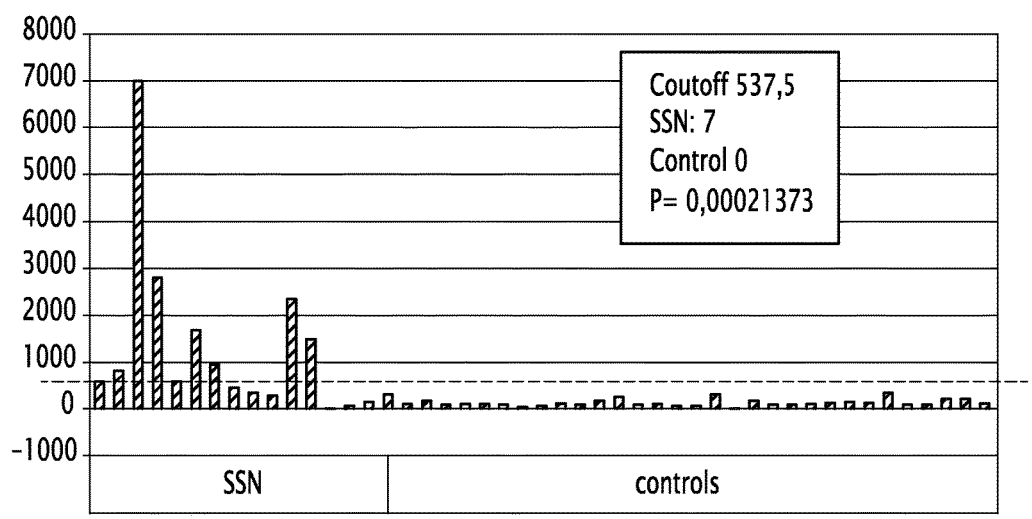
FIG. 2 illustrates the level of reactivity of 16 non paraneoplastic SNN and 30 controls on GRB10. The dotted line indicates the cut-off level. Protoarray assay.

Results 2.1. Protein Arrays 46 serum samples from 16 non paraneoplastic SNN (4 with associated dysimmune disorders) and 30 controls (15 healthy blood donors, 8 anti-Hu associated SNN and 7 non SNN neuropathies) were probed in the human ProtoArray v.4.2 (Invitrogen). Using the ProtoArray Prospector v5.0 software, CI p-value and z-score with the respective standard cut-off of 0.001 and 4, 442 immunoreactivities were identified as significantly different in the SNN group versus the control group. Using the following stringent criteria: reactivity restricted to the SNN group, level of reactivity >1010 in the SNN group and <900 in the control group and Z score >5, only two immunoreactivities distinguished significantly the SNN group from the control one: namely anti-FGFR3 (NCBI Reference Sequence: NP_000133.1) and GRB10 (NCBI Reference Sequence: NM_001001550.1) reactivity present in 7/16 patients respectively (cf. FIGS. 1 and 2). Six sera reacted with both FGFR3 and GRB10 and one with each of them respectively so that 8 sera reacted with at least one of them. The level of reactivity was wholly higher with FGFR3 than with GRB10.

2.2. ELISA with the FGFR3 Protein.

152 out of the 271 sera (patients or controls) were tested from 2 to 10 times, median 3, and used for adjusting the method.

Figure 3:
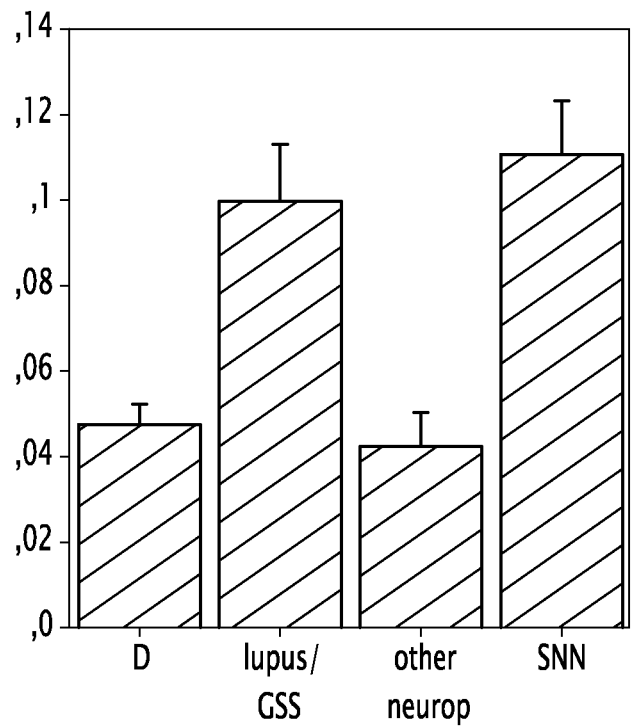
FIG. 3 is a histogram which illustrates the results of ELISA assays carried out on sera from patients suffering from autoimmune diseases or neuropathies, with the human FGFR3 399-806 aa peptide corresponding to the protein intracellular domain.

By an ANOVA test, the OD minus the blank value of sample sera was significantly higher in the sensory neuropathy and autoimmune disease groups comparatively to blood donors and patients with other peripheral neuropathy (FIG. 3). By the same test, patients with sensory neuropathy had higher normalized OD comparatively to the other groups (FIG. 4).

ROC curves were used to determine the cut-off values of the normalised OD and the index discriminating the SNN group from blood donors and other peripheral neuropathies with 100% specificity. A value of 0.13 for the normalized OD and 1.55 for the index were determined as the respective cut-off values. To be considered as positive for anti-FGFR3 antibodies both the normalized OD and the index values of a given serum had to be superior to the cut-off levels.

This allowed the identification of 14/104 patients with sensory neuropathy, 0/59 blood donors, 0/42 patients with other neuropathies and 5/56 patients with autoimmune diseases with FGFR3 antibodies (FIG. 5). The neuropathy in group III, was associated to an autoimmune context in 3/14 patients and diagnosed as possible or probable SNN in 13/14 cases the last patients having a form difficult to differentiate between SNN and P-CIDP. When going back to the clinical file of the 5 patients with autoimmune disease (group II), two of them proved to have trigeminal sensory neuronopathy, one sensory neuropathy in the four limbs, one chronic thoracic neuropathic pain and one no known neurological syndrome.

2.3. Dot Blot with FGFR3

To confirm the Elisa result by another method, the commercial FGFR3 antibody and two sera with patients with anti-FGFR3 antibody reacted by dot blot with the FGFR3 protein while sera from a blood donor did not (data not shown).

2.4. Elisa with FGFR1 and FGFR2 Proteins

As the FGFRs proteins share a high degree of homology, to test the possibility of serum cross immunoreactivity between FGFR3 and the other FGFRs, a sample of SNN, autoimmune disease and control sera were tested by Elisa with the FGFR1 and 2 recombinant proteins. FGFR4 was not tested as none of the SNN and control sera analysed by the protoarray method reacted with it. Four out of 13 sera positive for FGFR3 were found positive with FGFR1 while none of 14 sera negative for FGFR3 were positive for FGFR1. Concerning FRGF2, 2/7 sera positive for FGFR3 were positive for FGFR2 while none of 5 sera negative for FGFR3 were positive for FGFR2. Two sera reacted with the three proteins. These results show that although cross immunoreactivity may occur with FGFR 1 and 2, FGFR3 is more frequently recognized by autoantibodies in patients with sensory neuronopathy.

2.5. Expression of FGFR Proteins by Sensory Neurons In vitro.

As the patients with anti FGFR3 immunoreactivity were thought to have primary sensory neuron involvement that might be mediated to an auto-immunoreactivity directed toward FGFR3, the inventors checked that FGFR3 was expressed by dorsal root ganglia sensory neurons. By immunohistochemistry the FGFR3, 2 and 1 antibodies immunolabelled the cytoplasm of sensory neurons double labelled with the CRMP5 antibody while the FGFR5 antibody immunolabelled neuron nuclei (data not shown)).

2.6. Clinical Characteristics of the Neuropathy in Patients with FGFR3 Immunoreactivity.

As 17 of the 19 patients with FGFR3 antibody had sensory peripheral neuropathy (89%) multivariate logistic regression was used to compare the clinical and electrophysiological characteristics of their neuropathy with that of 36 patients without anti-FGFR3 antibody and non paraneoplastic sensory neuropathy and 31 patients with anti-Hu antibody and paraneoplastic SNN (see Table 1 below). The clinical and electrophysiological items analyzed in this study have been published elsewhere (Camdessanche J. P. et al., Brain 2009; 132:1723-1733).

TABLE 1 comparative clinical manifestation in patients with FGFR3
positive, FGFR3 negative and anti-Hu positive sensory neuropathy.

|  | FGFR3 positive | FGFR3 negative | Hu positive |
|---|---|---|---|
| Number | 19 | 38 | 31 |
| Age (M + SD) | 49.1 ± 15.6 | 60.5 ± 13.9 | 61.6 ± 11.3 |
| Sex (female) | 70% | 50% | 19% |
| Dysimmune contex | 42% | 26% | — |
| ONSET | | | |
| Acute | 17% | 12% | 36% |
| Subacute | 22% | 22% | 48% |
| Progressive | 61% | 66% | 16% |
| Face | 28% | 3% | 0% |
| Lower limbs | 56% | 71% | 58% |
| Upper limbs | 39% | 45% | 80% |
| FULL DEVEVELOPMENT | | | |
| Lower limbs | 78% | 95% | 97% |
| Upper limbs | 78% | 71% | 94% |
| Face | 28% | 11% | 13% |
| Trunk | 17% | 11% | 10% |
| Dysautonomia | 22% | 27% | 23% |
| Pain | 55% | 46% | 58% |
| Ataxia | 50% | 62% | 74% |
| Assymetry | 56% | 17% | 48% |
| CSF | | | |
| Normal | 50% | 44% | 0% |

Comparatively to patients without FGFR3 antibody and no paraneoplastic sensory neuropathy, patients with FGFR3 antibody tended to be younger (OR 0.97:0.93-1.02 95% CI; p=0.06), had more frequent trigeminal nerve involvement at onset of the neuropathy (OR 27.6:2.3-331.1 95% CI; p=0.009) and asymmetrical distribution of sensory loss at full development of the disorder (OR 8.7:1.9-41.2 95% CI; p=0.006). Comparatively to anti-Hu paraneoplastic SNN, patients with FGFR3 antibody were younger (OR 0.94:0.90-0.99 95% CI; p=0.02) and less frequently male (OR 0, 13:0.03-0.50 95% CI; p=0.003). Their neuropathy tended to have a more frequent slow progressive course (OR 7.2:0.9-62.9 95% CI; p=0.06) and less frequent ataxia (OR 0.04: 0.001-1.1 95% CI; p=0.06). Interestingly none of the electrophysiological criteria used in this study (number of abolished sensory action potentials or motor nerve conduction abnormalities) discriminated patients with FGFR3 antibody from those without whether their neuropathy was paraneoplastic or not. Nine patients with FGFR3 antibody underwent a spinal tap. A mild elevation of protein concentration was observed in 3, oligoclonal bands in 3 and cell reaction in 3. As a whole the CSF was abnormal in 5/9. A nerve biopsy was available in 4 patients (1 with Sjögren syndrome and 3 without known autoimmune context) and showed fiber loss without regenerating cluster consistent with a diagnosis of SNN in all of them. In one patient without autoimmune context, nerve vasculitis consisting of CD3+T lymphocytes was present in the epineurium.

2.7. Reactivity of Sera with HEK FGFR3 Transfected Cells.

Serum samples from four patients with sensory neuronopathy and anti-FGFR3 antibody detected by ELISA and four healthy blood donors were tested on transfected cells. The results are summarized in the table 2 below. Different patterns of reactivity were observed: some sera reacted with the full length protein and intracellular domain while others also reacted with TRK1 and 2. As a whole, the four sera reacted with the intracellular domain of the FGFR3 protein in concordance with the ELISA method which used the intracellular domain of the protein.

TABLE 2 immunoreactivity of the serum of four patients with
anti-FGFR3 antibody by ELISA on HEK 293 cells
transfected with the full length FGFR3, the
intracytoplasmic domain, TRK1 or TRK2 subunit
of the intracellular domain of FGFR3.

| sera | FL-FGFR3 | intracellular domain | TRK1 | TRK2 |
|---|---|---|---|---|
| Patient 1 | pos | pos | neg | neg |
| Patient 2 | pos | pos | neg | neg |
| Patient 3 | pos | pos | pos | pos |
| Patient 4 | neg | pos | neg | neg |
| Control 1 | neg | neg | neg | neg |
| Control 2 | neg | neg | neg | neg |
| Control 3 | neg | neg | neg | neg |
| Control 4 | neg | neg | neg | neg | pos: positive.
neg: negative.

2.8. Discussion

The inventors have identified FGFRs and their associated GRB proteins as potential target of IgG autoantibodies in patients with sensory neuronopathy (SNN).

Elisa and protein arrays using a peptide from the intracellular kinase domain of FGFR3 (amino acids 399-806) allowed identification of a group of patients with SSN (most of them without known associated autoimmune context) harbouring anti-FGFR3 antibodies. Immunocytochemistry performed on cells transfected with the full length FGFR3, the intracellular domain (amino acids 397-806), TRK1 or TRK2 confirms that the FGFR3 anti-sera reacted with the tyrosine kinase domain, although some sera also reacted with TRK1 or TRK2.

As a whole, the FGFR3 antibody associated neuropathy follows the criteria of probable SNN in 82% of cases according to published criteria in patients with available information (Camdessanche J. P. et al., Brain 2009; 132: 1723-1733), the others but one having sensory neurons involvement on clinical evaluation. In some patients, the sensory neuron disorder may present as small fibre neuropathy or trigeminal nerve neuropathy. Interestingly one patient for whom the diagnosis hesitated between CIDP and SNN and another one presenting with distal sensory neuropathy can be reallocated to a diagnosis of SNN because of the presence of FGFR3 antibody.

SNN may occur with lupus or Sjögren syndrome but the neuropathy frequently appears months or years before the autoimmune disorder becomes apparent while many cases of SNN never develop any autoimmune context even after a very protracted course. It is not established that when present the autoimmune disease is responsible for the neuropathy and most probably their co-occurrence results from the association of two autonomous autoimmune disorders. In this study, 47% of patients with FGFR3 antibodies have an autoimmune context including lupus or lupus anticoagulant, Sjögren syndrome, sclerodermy or unclassified autoimmune disorder. One patient had HIV infection. In the others, there was no known autoimmune context. Interestingly, in one of them a nerve biopsy disclosed vasculitis in the epinerium confirming that the disorder involves inflammatory mechanisms.

Therefore detection of FGFR3 antibodies early in the course of the neuropathy leads to ascribe the neuropathy to an otherwise undetected autoimmune disorder. There are to date no known biomarkers for non paraneoplastic SNN. The availability of such a diagnostic tool allows the identification of a group of patients who are currently considered as having an idiopathic disease and who can now be candidate to receive an immunological treatment.

The invention claimed is:

1. A method for treating a patient suffering from an acquired sensory neuronopathy who shows immunoreactivity toward a protein of the tyrosine kinase receptor family chosen from FGFR1, FGFR2 or FGFR3 and/or toward a GRB10 protein, which method comprises
   a) detecting in a biological sample of the patient immunoreactivity toward a protein of the tyrosine kinase receptor family chosen from FGFR1, FGFR2 or FGFR3 and/or toward a GRB10 protein; and
   b) administering to the patient at least an immunosuppressant and/or immunomodulator compound(s), or a pharmaceutical composition comprising said compound(s).

2. The method of claim 1, wherein the immunosuppressant compound is chosen from the group consisting of tacrolimus (CAS number 104987-11-3), cyclosporine (CAS number 59865-13-3), methotrexate (CAS number 59-05-2), glucocorticoids, cyclophosphamide (CAS number 50-18-0), azathioprine (CAS number 446-86-6), mycophenolate mofetil (CAS number 24280-93-1), anti-CD20 antibodies and fingolimod (CAS number 162359-55-9).

3. The method of claim 1, wherein the protein of the tyrosine kinase receptor family is chosen from the group consisting of i) FGFR3, ii) a protein which comprises or consists of the intracellular kinase domain of FGFR3, iii) a protein which comprises or consists of the TRK1 subunit of the intracellular kinase domain of FGFR3, and iv) a protein which comprises or consists of the TRK2 subunit of the intracellular kinase domain of FGFR3.

4. The method of claim 1, wherein the proteins toward which immunoreactivity is detected are i) a protein chosen from the group consisting of FGFR3, a protein which comprises or consists of the intracellular kinase domain of FGFR3, a protein which comprises or consists of the TRK1 subunit of the intracellular kinase domain of FGFR3, and a protein which comprises or consists of the TRK2 subunit of the intracellular kinase domain of FGFR3, and ii) GRB10.

5. An analytical method comprising
   i) obtaining a biological sample from a patient having an acquired sensory neuronopathy and
   ii) detecting, in the biological sample, antibodies toward a protein of the tyrosine kinase receptor family chosen from FGFR1, FGFR2 or FGFR3 and/or toward a GRB10 protein.

* * * * *